(12) United States Patent
Nudelman et al.

(10) Patent No.: US 8,222,296 B2
(45) Date of Patent: Jul. 17, 2012

(54) CONJUGATES COMPRISING A GABA- OR GLYCINE COMPOUND, PHARMACEUTICAL COMPOSITIONS AND COMBINATIONS THEREOF AND THEIR USE IN TREATING CNS DISORDERS

(75) Inventors: Abraham Nudelman, Rechovot (IL); Ada Rephaeli, Herzlia (IL); Irit Gil-Ad, Herzlia (IL); Abraham Weizman, Tel-Aviv (IL); Ran Lifshitz, Ramat-Gan (IL); Ilan Winkler, Lapid (IL)

(73) Assignees: Ramot at Tel-Aviv University Ltd., Tel-Aviv (IL); Bar-Ilan University, Ramat-Gan (IL); BioLineRX Ltd., Jerusalem (IL)

( * ) Notice: Subject to any disclaimer, the term of this patent is extended or adjusted under 35 U.S.C. 154(b) by 520 days.

(21) Appl. No.: 12/373,542

(22) PCT Filed: Jul. 17, 2007

(86) PCT No.: PCT/IL2007/000902
§ 371 (c)(1),
(2), (4) Date: Jan. 13, 2009

(87) PCT Pub. No.: WO2008/010222
PCT Pub. Date: Jan. 24, 2008

(65) Prior Publication Data
US 2009/0304584 A1    Dec. 10, 2009

Related U.S. Application Data

(60) Provisional application No. 60/831,192, filed on Jul. 17, 2006, provisional application No. 60/831,195, filed on Jul. 17, 2006.

(51) Int. Cl.
*A61K 31/22* (2006.01)
*C07C 69/00* (2006.01)
(52) U.S. Cl. .................. 514/551; 560/142; 560/130
(58) Field of Classification Search .................. 560/130, 560/142; 514/551
See application file for complete search history.

(56) References Cited

U.S. PATENT DOCUMENTS

| | | | |
|---|---|---|---|
| 2,914,528 A | 11/1959 | Craig | |
| 2,944,053 A | 7/1960 | Edgerton | |
| 2,969,358 A | 1/1961 | Cusic | |
| 3,227,708 A | 1/1966 | Yale et al. | |
| 3,956,493 A | 5/1976 | Yale | |
| 3,966,930 A | 6/1976 | Buus et al. | |
| 3,978,216 A | 8/1976 | Fuxe | |
| 4,153,694 A | 5/1979 | Buus et al. | |
| 4,629,691 A | 12/1986 | Collins et al. | |
| 4,818,936 A | 4/1989 | Kemlo | |
| 5,051,448 A | 9/1991 | Shashoua | |
| 5,145,684 A | 9/1992 | Liversidge et al. | |
| 5,525,727 A | 6/1996 | Bodor et al. | |
| 5,828,405 A | 10/1998 | Vanier et al. | |
| 5,966,673 A | 10/1999 | Shannon, Sr. | |
| 5,983,238 A | 11/1999 | Becker et al. | |
| 5,994,392 A | 11/1999 | Shashoua et al. | |
| 6,020,954 A | 2/2000 | Aggarwal | |
| 6,121,325 A | 9/2000 | Chen et al. | |
| 6,197,764 B1 | 3/2001 | Bradley et al. | |
| 6,239,867 B1 | 5/2001 | Aggarwal | |
| 6,294,562 B1 | 9/2001 | Stilz et al. | |
| 6,304,853 B1 | 10/2001 | Malnekoff | |
| 6,381,510 B1 | 4/2002 | Amidhozour et al. | |
| 6,569,853 B1 | 5/2003 | Borisy et al. | |
| 7,544,681 B2 | 6/2009 | Nudelman et al. | |
| 7,598,239 B2 | 10/2009 | Nudelman et al. | |
| 7,619,006 B2 | 11/2009 | Nudelman et al. | |
| 7,939,525 B2 | 5/2011 | Nudelman et al. | |
| 2001/0024532 A1 | 9/2001 | Malnekoff | |
| 2002/0010208 A1 | 1/2002 | Shashoua et al. | |
| 2002/0021439 A1 | 2/2002 | Priestley et al. | |
| 2002/0052170 A1 | 5/2002 | Holloway | |
| 2003/0065586 A1 | 4/2003 | Shaftel et al. | |
| 2003/0115079 A1 | 6/2003 | Rapaport | |
| 2004/0068417 A1 | 4/2004 | Sevdermish | |
| 2004/0092504 A1 | 5/2004 | Benja-Athon | |
| 2004/0242570 A1 | 12/2004 | Nudelman et al. | |
| 2005/0149369 A1 | 7/2005 | Sevdermish | |
| 2006/0046967 A1* | 3/2006 | Satyam | ............ 514/19 |
| 2006/0058219 A1 | 3/2006 | Miller | |
| 2006/0142181 A1 | 6/2006 | Miller | |
| 2007/0099977 A1 | 5/2007 | Nudelman et al. | |
| 2007/0197514 A1 | 8/2007 | Nudelman et al. | |
| 2007/0219181 A1 | 9/2007 | Kimura et al. | |
| 2008/0108606 A1 | 5/2008 | Nudelman et al. | |

(Continued)

FOREIGN PATENT DOCUMENTS
CA          2461663           4/2003
(Continued)

OTHER PUBLICATIONS

Bousquet et al. "Synthesis, Physical properties, toxicological studies and bioavailability of L-pyroglutamic and L-glutamic acid esters of paracetamol as potentially useful prodrugs," J. Pharm. Pharmacol. 1996, vol. 48, pp. 479-485.*
Response Dated Feb. 9, 2011 to Office Action of Aug. 11, 2010 From the State Intellectual Property Office of the People's Republic of China Re. Application No. 200810190781.X.
Response Dated Nov. 28, 2010 to Office Action of Jul. 27, 2010 From the Israel Patent Office Re.: Application No. 199877.
Translation of Office Action Dated Aug. 11, 2010 From the State Intellectual Property Office of the People's Republic of China Re. Application No. 200810190781.X.

(Continued)

*Primary Examiner* — Shengjun Wang

(57) ABSTRACT

Conjugates of a gamma-aminobutyric acid (GABA) compound or a glycine compound and an analgesic drug are disclosed. Further disclosed are pharmaceutical compositions containing these conjugates and uses thereof in the treatment of CNS-associated diseases or disorders, optionally in combination with a psychotropic drug.

23 Claims, No Drawings

U.S. PATENT DOCUMENTS

| | | | |
|---|---|---|---|
| 2009/0215809 | A1 | 8/2009 | Yao et al. |
| 2009/0298814 | A1 | 12/2009 | Nudelman et al. |
| 2009/0304584 | A1 | 12/2009 | Nudelman et al. |
| 2010/0063034 | A1 | 3/2010 | Nudelman et al. |
| 2010/0120755 | A1 | 5/2010 | Nudelman et al. |
| 2010/0204469 | A1 | 8/2010 | Nudelman et al. |
| 2011/0312948 | A1 | 12/2011 | Nudelman et al. |

FOREIGN PATENT DOCUMENTS

| | | |
|---|---|---|
| CN | 1596141 | 3/2005 |
| EP | 0361485 | 4/1990 |
| ES | 8707175 | 10/1987 |
| GB | 829246 | 3/1960 |
| GB | 1460713 | 5/1978 |
| GB | 1514312 | 6/1978 |
| GB | 2159636 | 12/1985 |
| GB | 2188630 | 10/1987 |
| GB | 2358541 | 7/2001 |
| JP | 50-025574 | 3/1975 |
| JP | 53-050185 | 5/1978 |
| JP | 62-501991 | 8/1987 |
| JP | 62-240660 | 10/1987 |
| JP | 02-128564 | 5/1990 |
| JP | 02128564 | 5/1990 |
| JP | 02-188527 | 7/1990 |
| JP | 03-017076 | 2/1991 |
| JP | 03017076 | 2/1991 |
| JP | 60-72868 | 3/1994 |
| JP | 60-072868 | 3/1994 |
| JP | 10-059948 | 3/1998 |
| JP | 11-506723 | 6/1999 |
| JP | 2000-020681 | 1/2000 |
| JP | 2000020681 | 1/2000 |
| JP | 2001-501965 | 2/2001 |
| JP | 2001-201454 | 7/2001 |
| JP | 2001201454 | 7/2001 |
| JP | 2001-519754 | 10/2001 |
| JP | 2005-503423 | 2/2005 |
| JP | 2005-097120 | 4/2005 |
| WO | WO 86/04991 | 8/1986 |
| WO | WO 93/12496 | 6/1993 |
| WO | WO 96/40687 | 12/1996 |
| WO | WO 97/02819 | 1/1997 |
| WO | WO 97/44063 | 11/1997 |
| WO | WO 98/17678 | 4/1998 |
| WO | WO 98/52898 | 11/1998 |
| WO | WO 99/26661 | 6/1999 |
| WO | WO 01/91011 | 11/2001 |
| WO | WO 02/28881 | 4/2002 |
| WO | WO 02/43652 | 6/2002 |
| WO | WO 03/026563 | 4/2003 |
| WO | WO 03/061656 | 7/2003 |
| WO | WO 03/062942 | 7/2003 |
| WO | WO 2005/032474 | 4/2005 |
| WO | WO 2005/092392 | 10/2005 |
| WO | WO 2006/027711 | 3/2006 |
| WO | WO 2006/058219 | 6/2006 |
| WO | WO 2006/131923 | 12/2006 |
| WO | WO 2007/050318 | 5/2007 |
| WO | WO 2007/139818 | 12/2007 |
| WO | WO 2008/010222 | 1/2008 |
| WO | WO 2008/010223 | 1/2008 |
| WO | WO 2009/101616 | 8/2009 |
| WO | WO 2011/104637 | 9/2011 |
| WO | WO 2012/038963 | 3/2012 |

OTHER PUBLICATIONS

Communication Pursuant to Article 94(3) EPC Dated Apr. 11, 2011 From the European Patent Office Re. Application No. 09711260.1.
Office Action Dated Jun. 6, 2010 From the Israeli Patent Office Re.: Application No. 161083 and Its Translation Into English.
Response Dated Jun. 23, 2010 to Notice of the Reason for Rejection of Mar. 26, 2010 From the Korean Intellectual Property Office Re.: Application No. 2004-7004581.
Response Dated Jun. 23, 2010 to Notice of the Reason for Rejection of Feb. 24, 2010 From the Korean Intellectual Property Office Re.: Application No. 2009-7024590.
Interview Summary Dated Jan. 27, 2011 From the US Patent and Trademark Office Re.: U.S. Appl. No. 12/585,021.
Notice of Allowance Dated Mar. 21, 2011 From the US Patent and Trademark Office Re.: U.S. Appl. No. 12/585,021.
Official Action Dated Jul. 12, 2011 From the US Patent and Trademark Office Re. U.S. Appl. No. 11/921,578.
Response Dated Mar. 9, 2011 to Official Action of Dec. 14, 2010 From the US Patent and Trademark Office Re.: U.S. Appl. No. 12/585,021.
Response Dated Jun. 16, 2011 to Communication Pursuant to Article 94(3) EPC of Dec. 16, 2010 From the European Patent Office Re. Application No. 02772790.8.
Official Action Dated Mar. 14, 2011 From the US Patent and Trademark Office Re. U.S. Appl. No. 12/764,124.
Response Dated Jul. 6, 2011 to Official Action of Mar. 14, 2011 From the US Patent and Trademark Office Re. U.S. Appl. No. 12/764,124.
International Preliminary Report on Patentability Dated Aug. 26, 2010 From the International Bureau of WIPO Re. Re. Application No. PCT/IL2009/000158.
Office Action of Jul. 27, 2010 From the Israel Patent Office Re.: Application No. 199877 and Its Translation Into English.
Communication Pursuant to Article 94(3) EPC Dated Dec. 16, 2010 From the European Patent Office Re. Application No. 02772790.8.
Communication Pursuant to Article 94(3) EPC Dated Nov. 24, 2010 From the European Patent Office Re. Application No. 07789958.1.
Requisition by the Examiner Dated Nov. 8, 2010 From the Canadian Intellectual Property Office Re. Application No. 2,461,663.
Response Dated Nov. 8, 2010 to Office Action of Jul. 12, 2010 From the State Intellectual Property Office of the People's Republic of China Re. Application No. 200780033294.6.
Response Dated Nov. 16, 2010 to Examination Report of Aug. 25, 2010 From the Instituto Mexicano de la Propriedad Industrial Re. Application No. PA/a/2004/002912.
Response Dated Dec. 20, 2010 to Notice of the Reason for Rejection of Oct. 28, 2010 From the Korean Itellectual property Office Re. Application No. 2010-7016372.
Translation of Final Notice of the Reason for Rejection Dated Nov. 24, 2010 From the Korean Intellectual Property Office Re.: Application No. 2009-7024590.
Ogiso et al. "Pharmacokinetic Analysis of Phenytoin and Its Derivatives in Plasma and Brain in Rats", Biological and Pharmaceutical Bulletin, XP002613683, 16(10): 1025-1030, Oct. 1, 1993.
European Search Report and the European Search Opinion Dated Dec. 30, 2010 From the European Patent Office Re. Application No. 10182948.9.
Official Action Dated Jan. 6, 2011 From the US Patent and Trademark Office Re. U.S. Appl. No. 12/656,048.
Carducci et al. "Phenylbutyrate Induces Apoptosis in Human Prostate Cancer and Is More Potent Than Phenylacetate", Clinical Cancer Research, XP002613699, 2(2): 379-387, 1996. Abstract.
Coradini et al. "Effect of Sodium Butyrate on Human Breast Cancer Cell Lines", Cell Proliferation, XP002613698, 30(3-4) Mar. 1997. Abstract.
Luo et al. "Comparative Pharmacokinetic Analysis of Fluphenazine and Four Ester Prodrugs", Pharmaceutical Research, XP008130430, 14(11 Suppl.): S360, # 2441, Nov. 1997. & Annual Meeting of the American Association of Pharmaceutical Scientists, Boston, MA, USA, Nov. 2-6, 1997.
Milovic "Effect of Structural Analogues of Propionate and Butyrate on Colon Cancer Cell Growth", International Journal of Colorectal Disease, XP002613700, 15(5-6): 264-270, 2000. Abstract, p. 267, Table 2.
Velázquez et al. "Butyrate Inhibits Seeding and Growth of Colorectal Metastases to the Liver in Mice", Surgery, XP005473855, 120(2): 440-448, Aug. 1, 1996. Abstract.
Communication Pursuant to Rules 70(2) and 70a(2) EPC Dated Jan. 31, 2011 From the European Patent Office Re. Application No. 10182948.9.
Response Dated Jan. 18, 2011 to Notice of Reason for Rejection of Nov. 2, 2010 From the Japanese Patent Office Re. Application No. 2007-504560.

International Search Report and the Written Opinion Dated Dec. 3, 2007 From the International Searching Authority Re.: Application No. PCT/IL2006/000666.
Response Dated Mar. 3, 2010 to Official Action of Feb. 16, 2010 From the US Patent and Trademark Office Re.: U.S. Appl. No. 12/585,021.
BioLineRx "BioLineRx Announces Positive Topline Results for BL-1020, A First in Class GABA Enhanced Antipsychotic for the Treatment of Schizophrenia. BL-1020 Meets Primary and Secondary Efficacy Endpoints From the Pahase 2b EAGLE Trial", BioLine Rx, 4 P., Sep. 14, 2009.
Sakamoto et al. "Studies on Prodrugs. VI. Preparation and Characterization of 95-Substituted 2-Oxo-1,3-Dioxol-4-yl)Methyl Esters of Mecillinam", Chemical and Pharmaceutical Bulletin, 35(2): 642-646, 1987. Abstract.
International Search Report and the Written Opinion Dated Mar. 30, 2011 From the International Searching Authority Re. Application No. PCT/IL2010/01041.
Office Action Dated Mar. 2, 2011 From the Israel Patent Office Re. Application No. 196538 and Its Translation Into English.
Interview Summary Dated May 6, 2011 From the US Patent and Trademark Office Re. U.S. Appl. No. 12/656,048.
"New Edition of Pharmaceutics", People's Hygiene Publishing House, 14: 178, 1998. Abstract in Chinese Only!
Chinese Official Action Dated Aug. 8, 2008 From Patent Office of the Peoples Republic of China Re.: Application No. 02823600.9.
Communication Pursuant to Article 96(2) EPC Dated Nov. 24, 2006 From the European Patent Office Re.: Application No. 02772790.8.
Communication Under Rule 112 EPC Dated Oct. 2, 2007 From the European Patent Office Re.: Application No. 05718914.4.
Examiner's Report Dated May 2, 2007 From the Australian Government Re.: Application No. 2004201240.
Examiner's Report Dated May 23, 2007 From the Government of India Patent Office Re.: Application No. 642/CHENP/2004-SPS.
International Preliminary Examination Report Dated Oct. 12, 2006 From the International Searching Authority by Patent Cooperation Treaty Re.: Application No. PCT/IL2005/000341.
International Search Report Dated Jul. 11, 2003 From the International Searching Authority Re.: Application No. PCT/IL02/00795.
International Search Report Dated Feb. 12, 2008 From the International Searching Authority Re.: Application No. PCT/IL2007/000903.
International Search Report Dated Feb. 13, 2008 From the International Searching Authority Re.: Application No. PCT/IL2007/000902.
International Search Report Dated Aug. 23, 2006 From the International Searching Authority Re.: Application No. PCT/IL2005/000341.
Notice of Allowance Dated Mar. 11, 2008 From the US Patent and Trademark Office Re.: U.S. Appl. No. 10/808,541.
Office Action Dated Feb. 1, 2007 From the US Patent and Trademark Office Re.: U.S. Appl. No. 10/808,541.
Office Action Dated May 9, 2008 From the US Patent Office Re.: U.S. Appl. No. 11/636,599.
Office Action Dated May 16, 2008 From the US Patent Office Re.: U.S. Appl. No. 11/636,594.
Office Action Dated Apr. 17, 2008 From the US Patent and Trademark Office Re.: U.S. Appl. No. 11/636,594.
Office Action Dated Jun. 19, 2008 From the US Patent Office Re.: U.S. Appl. No. 11/636,599.
Office Action Dated Jul. 25, 2006 From the US Patent and Trademark Office Re.: U.S. Appl. No. 10/808,541.
Office Action Dated Mar. 30, 2006 From the US Patent and Trademark Office Re.: U.S. Appl. No. 10/808,541.
Official Action Dated Sep. 9, 2005 From the Patent Office of the People's Republic of China Re.: Application No. 02823600.9 and Its Translation Into English.
Official Action Dated Feb. 14, 2008 From the Government of India Patent Office Re.: Application No. 642/CHENP/2004-SPS.
Official Action Dated May 15, 2008 From the Government of India Patent Office Re.: Application No. 642/CHENP/2004-SPS.
Official Action Dated Sep. 16, 2008 From the US Patent Office Re.: U.S. Appl. No. 12/005,342.

Official Action Dated Oct. 31, 2008 From the US Patent Office Re.: U.S. Appl. No. 12/005,342.
Partial International Search Report Jun. 13, 2006 From the International Searching Authority Re.: Application No. PCT/IL2005/000341.
Partial International Search Report Dated Nov. 20, 2007 From the International Searching Authority Re.: Application No. PCT/IL2007/000902.
Partial International Search Report Dated Nov. 27, 2007 From the International Searching Authority Re.: Application No. PCT/IL2007/000903.
Supplementary European Search Report Dated Apr. 25, 2006 From the European Patent Office Re.: Application No. 02772790.8.
Written Opinion Dated Feb. 12, 2008 From the International Searching Authority Re.: Application No. PCT/IL2007/000903.
Written Opinion Dated Feb. 13, 2008 From the International Searching Authority Re.: Application No. PCT/IL2007/000902.
Written Opinion Dated Aug. 23, 2006 From the international Searching Authority Re.: Application No. PCT/IL2005/000341.
Budavari et al. "The Merck Index", Merck & Co., USA, 12th Ed., 1996, P.THER-8, First Col., 6th Line From the Bottom, 2nd Col., Line 13.. P.THER-8, First Col., 6th Line From the Bottom, 2nd Col., Line 13.
Budavari et al. "The Merck Index", Merck & Co., USA, 12th Ed, 1996, p. 1260. p. 1260, § 1.
Budavari et al. "The Merck Index", Merck & Co., USA, 12th Ed., 1996, p. 1246. p. 1246, Last §.
Capasso et al. "Anticonvulsive Activity of a New GABA Mimetic Drug", European Neuropsychopharmacology, 7: 57-63, 1997.
Fingl et al. "General Principles", The Pharmacological Basis of Therapeutics, Chap.1: 1-46, 1975.
Geyer et al. "Animal Behavior Models of the Mechanisms Underlying Antipsychotic Atypicality", Progress in Neuro-Psychopharmacology & Biological Psychiatry, 27: 1071-1079, 2003.
Hadad et al. "Pharmacokinetic Analysis and Antiepileptic Activity of N-Valproyl Derivatives of GABA and Glycine", Pharmaceutical Research, 112(6): 905-910, 1995.
Köpf-Maier et al. "An Organoid Culture Assay (OCA) for Determining the Drug Sensitivity of human Tumors", Int. J. Cancer, 51: 99-107, 1992.
Lloyd et al. "The Potential Use of GABA Agonists in Psychiatric Disorders: Evidence From Studies With Progabide in Animal Models and Clinical Trials", Pharmacology, Biochemistry & Behavior, 18: 957-966, 1983.
McCaffrey et al. "A Rapid Fluorometric DNA Assay for the Measurement of Cell Density and Proliferation In Vitro", In Vitro Cellular Development Biology, 24(3): 247-252, 1988. Abstract.
Nicoletti et al. "A Rapid and Simple Method for Measuring Thymocyte Apoptosis by Propidium Iodide Staining and Flow Cytometry", Journal of Immunological Methods, 139: 271-279, 1991.
Nordenberg et al. "Effects of Psychotropic Drugs on Cell Proliferation and Differentiation", Biochemical Pharmacology, 58: 1229-1236, 1999.
Pouzet et al. "Effects of the 5-HT7 Receptor Antagonist SB-258741 in Animal Models for Schizophrenia", Pharmacology, Biochemistry and Behavior, 71: 655-665, 2002.
Quadri et al. "Effects of Centrally Acting Drugs on Serum Prolactin Levels in Rhesus Monkeys", Neuroendocrinology, 27(3-4): 136-147, 1978. Abstract.
Rephaeli et al. "Observation of Sequence-Dependent Interaction Between Prodrugs of Carboxylic-Acid-Esters and Doxorubicin in Cancer Cells", Proceedings of the American Association for Cancer Research, Annual Meeting, 40: 592-, 1999. Abstract. & 90th Annual Meeting of the American Association for Cancer Research, Philadelphia, PA, USA, 1999.
Scriba "Phenytoin-Lipid Conjugates as Potential Prodrugs of Phenytoin", Archiv der Pharmazie, VCH—Verlagsgesellschaft MBH, Weinheim, DE, 326(8): 477-481, 1993. Scheme 1, p. 147.
Scriba et al "Anticonvulsant Activity of Phenytoin-Lipid Conjugates, A New Class of Phenytoin Prodrugs"—Journal of Pharmaceutical Pharmacology, 47: 197-203, 1996. Scheme 1, p. 198, Abstract.

Scriba et al. "Synthesis and Anticovulsant Activity of N-Benzyloxycarbonyl-Amino Acid Prodrugs of Phenytoin", Journal of Pharmacy and Pharmacology, 51: 549-553, 1999.
Shalitin et al. "The Effect of Angiotensin II on Myosin Heavy Chain Expression in Cultured Myocardial Cells", In Vitro Cellular Development Biology—Animal, 32: 573-578, 1996.
Toth "A Novel Chemical Approach to Drug Delivery: Lipidic Amino Acid Conjugates", Journal of Drug Targeting, 2(3): 217-239, 1994. p. 223, col. II, 3rd §.
Wolffe "Transcriptional Control. Sinful Repression", Nature, 387: 16017, 1997.
Worms et al. "Dopamine-Like Activities of an Aminopyridazinde Derivative, CM 30366: A Behavioural Study", Naunyn-Schmiedeberg's Archives of Pharmacology, 334: 246-252, 1986.
Yogev-Falach et al. "The Importance of Propargylamine Moiety in the Anti-Parkinson Drug Rasagiline and Its Derivatives in MAPK-Dependent Amyloid Precursor Protein Processing", The FASEB Journal, 17: 2325-2327, 2003. Abstract.
Zaugg et al. "Modification of Hemoglobin With Analogs of Aspirin", The Journal of Biological Chemistry, 255(7): 2816-2821, 1980.
Examination Report Dated May 30, 2011 From the Instituto Mexicano de la Propriedad Industrial Re. Application No. PA/a/2004/002912 and Its Summary in English.
Notice of Allowance Dated May 29, 2009 From the US Patent and Trademark Office Re.: U.S. Appl. No. 12/005,342.
Office Action Dated May 17, 2011 From the Israel Patent Office Re.: Application No. 187892 and Its Translation Into English.
Response Dated May 1, 2006 to Official Action of Mar. 30, 2006 From the US Patent and Trademark Office Re.: U.S. Appl. No. 10/808,541.
Response Dated Dec. 3, 2007 to Official Action of Feb. 1, 2007 From the US Patent and Trademark Office Re.: U.S. Appl. No. 10/808,541.
Response Dated Oct. 13, 2008 to Official Action of Sep. 16, 2008 From the US Patent and Trademark Office Re.: U.S. Appl. No. 12/005,342.
Response Dated Nov. 15, 2006 to Official Action of Jul. 25, 2006 From the US Patent and Trademark Office Re.: U.S. Appl. No. 10/808,541.
Response Dated Feb. 24, 2009 to Official Action of Oct. 31, 2008 From the US Patent and Trademark Office Re.: U.S. Appl. No. 12/005,342.
Supplemental Response Dated Mar. 31, 2009 to Response of Feb. 24, 2009 From the US Patent and Trademark Office Re.: U.S. Appl. No. 12/005,342.
Official Action Dated Aug. 5, 2011 From the US Patent and Trademark Office Re. U.S. Appl. No. 12/764,124.
Examiner's Report Dated May 2, 2007 From the Australian Government, IP Australia Re.: Application No. 2004201240.
Examiner's Report Dated Oct. 21, 2010 From the Australian Government, IP Australia Re. Application No. 2006256369.
Examiner's Report Dated Feb. 24, 2010 From the Australian Government, IP Australia Re.: Application No. 2008243147.
Notice of the Reason for Rejection Dated Mar. 26, 2010 From the Korean Intellectual Property Office Re.: Application No. 2004-7004581. Korean Only.
Office Action Dated Aug. 8, 2008 From the Patent Office of the People's Republic of China Re.: Application No. 02823600.9.
Office Action Dated Sep. 9, 2005 From the Patent Office of the People's Republic of China Re.: Application No. 02823600.9 and Its Translation Into English.
Office Action Dated Feb. 14, 2008 From the Government of India Patent Office Re.: Application No. 642/CHENP/2004-SPS.
Office Action Dated May 15, 2008 From the Government of India Patent Office Re.: Application No. 642/CHENP/2004-SPS.
Official Action Dated May 9, 2008 From the US Patent and Trademark Office Re.: U.S. Appl. No. 11/636,599.
Official Action Dated May 16, 2008 From the US Patent and Trademark Office Re.: U.S. Appl. No. 11/636,594.
Official Action Dated Sep. 16, 2008 From the US Patent and Trademark Office Re.: U.S. Appl. No. 12/005,342.
Official Action Dated Apr. 17, 2008 From the US Patent and Trademark Office Re.: U.S. Appl. No. 11/636,594.

Official Action Dated Jun. 17, 2010 From the US Patent and Trademark Office Re.: U.S. Appl. No. 12/585,021.
Official Action Dated Mar. 30, 2006 From the US Patent and Trademark Office Re.: U.S. Appl. No. 10/808,541.
Response Dated Oct. 5, 2010 to Official Action of Jun. 17, 2010 From the US Patent and Trademark Office Re.: U.S. Appl. No. 12/585,021.
Translation of Notice of Reason for Rejection Dated Feb. 10, 2009 From the Japanese Patent Office Re.: Application No. 2003-530202.
Prasad "Butyric Acid: A Small Fatty Acid With Diverse Biological Functions", Life Science, 27(15): 1351-1358, 1980.
Sakamoto et al. "Studies on Prodrugs. VI. Preparation and Characterization of 95-Substituted 2-Oxo-1,3-Dioxol-4-yl)Methyl Esters of Mecillinam", Chemical and Pharmaceutical Bulletin, 35(2): 642-646, 1987. Abstract.
Vezin et al. "Biological Active Poly(N-Metacryloyl-ω-Amino Acid) Esters of Fluphenazine and Their Duration of Activity", Journal of Pharmacy and Pharmacology, British Pharmacology Conference 1979, 31(Suppl.): 63P, 1979.
Translation of Notice of Final Rejection Dated May 30, 2011 From the Korean Intellectual Property Office Re. Application No. 2010-7016372.
Translation of Notice of Final Rejection Dated May 30, 2011 From the Korean Intellectual Property Office Re.: Application No. 2009-7024590.
Translation of Office Action Dated Jul. 12, 2010 From the State Intellectual Property Office of the People's Republic of China Re. Application No. 200780033294.6.
Response Dated Oct. 3, 2011 to Examination Report of Jun. 8, 2011 From the Instituto Mexicano de la Propriedad Industrial Re. Application No. MX/a/2007/015511.
Response Dated Mar. 22, 2011 to Final Notice of the Reason for Rejection of Nov. 24, 2010 From the Korean Intellectual Property Office Re.: Application No. 2009-7024590.
Response Dated Mar. 24, 2011 to Communication Pursuant to Article 94(3) EPC of Nov. 24, 2010 From the European Patent Office Re. Application No. 07789958.1.
Response Dated Jun. 6, 2010 to Office Action of Jan. 29, 2010 From the State Property Office of the People's Republic of China Re.: Application No. 200680029378.8.
Examination Report Dated Jun. 8, 2011 From the Instituto Mexicano de la Propriedad Industrial Re. Application No. MX/a/2007/015511 and Its Summary Into English.
Response Dated Feb. 25, 2011 to Official Action of Aug. 25, 2010 From the US Patent and Trademark Office Re. U.S. Appl. No. 12/764,124.
Official Action Dated Aug. 25, 2010 From the US Patent and Trademark Office Re. U.S. Appl. No. 12/764,124.
Response Dated Sep. 1, 2010 to Office Action of Apr. 25, 2010 From the Israel Patent Office Re.: Application No. 187892.
Office Action Dated Aug. 23, 2010 From the Israel Patent Office Re. Application No. 203058 and Its Translation Into English.
Response Dated Sep. 18, 2011 to Examination Report of Jun. 16, 2011 From the Instituto Mexicano de la Propriedad Industrial Re. Application No. PA/a/2006/010924.
Examination Report Dated Aug. 25, 2010 From the Instituto Mexicano de la Propriedad Industrial Re. Application No. PA/a/2004/002912 and its Summary in English.
Communication Pursuant to Article 94(3) Dated Apr. 2, 2008 From the European Patent Office Re.: Application No. 06756205.8.
Translation of Notice of the Reason for Rejection Dated Feb. 24, 2010 From the Korean Intellectual Property Office Re.: Application No. 2009-7024590.
Translation of Office Action Dated Jan. 29, 2010 From the State Intellectual Property Office of the People's Republic of China Re.: Application No. 200680029378.8.
Translation of Notice of the Reason for Rejection Dated Mar. 26, 2010 From the Korean Intellectual Property Office Re.: Application No. 2004-7004581.
Luo "Pharmacokinetic Studies of Fluphenazine and Four Ester Prodrugs", A Thesis Submitted to the College of Graduate Studies and Research in Partial Fulfillment of the Requirements for the Degree of Doctor of Philosophy in the College of Pharmacy and Nutrition, University Saskatchewan, Saskatoon, Saskatchewan, Canada, p. 1-171, 1999.
Office Action Dated Feb. 27, 2009 From the Israeli Patent Office Re.: Application No. 161083 and Its Translation Into English.
Official Action Dated Feb. 17, 2009 From the US Patent and Trademark Office Re.: U.S. Appl. No. 11/636,599.
Degrand et al. "Synthesis of Nitroxides for Use as Procationic Labels and Their Incorporation Into Nafion Films", The Journal of Organic Chemistry, 58(9): 2573-2577, 1993.
Examination Report Dated Jun. 16, 2011 From the Instituto Mexicano de la Propriedad Industrial Re. Application No. PA/a/2006/010924.
Office Action Dated Mar. 2, 2011 From the Israeli Patent Office Re. Application No. 196538.
Response Dated Aug. 2, 2011 to Office Action of Mar. 2, 2011 From the Israeli Patent Office Re. Application No. 196538.
Response Dated Jul. 24, 2011 to Communication Pursuant to Article 94(3) EPC of Apr. 11, 2011 From the European Patent Office Re. Application No. 09711260.1.
Response Dated Jul. 26, 2011 to Official Action of Mar. 14, 2011 From the US Patent and Trademark Office Re. U.S. Appl. No. 12/764,124.
Response Dated Jul. 26 to Communication Pursuant to Rules 70(2) and 70a(2) EPC of Jan. 31, 2011 From the European Patent Office Re. Application No. 10182948.9.
Response Dated Feb. 23, 2011 to Examiner's Report of Feb. 24, 2010 From the Australian Government, IP Australia Re.: Application No. 2008243147.
Office Action Dated Apr. 25, 2010 From the Israel Patent Office Re.: Application No. 187892 and Its Translation Into English.
English Summary of Examination Report Dated Sep. 4, 2007 From the Instituto Mexicano de la Propriedad Industrial Re. Application No. PA/a/2004/002912.
Examination Report Dated Sep. 20, 2010 From the Instituto Mexicano der la Propriedad Industrial Re. Application No. MX/a/2007/015511 and Its Translation Into English.
Office Action Dated Jun. 24, 2011 From the State Intellectual Property Office of the People's Republic of China Re. Application No. 200780033294.6 and Its Translation Into English.
Response Dated May 5, 2011 to Requisition by the Examiner of Nov. 8, 2010 From the Canadian Intellectual Property Office Re. Application No. 2,461,663.
Response Dated Jun. 6, 2011 to Official Action of Jan. 6, 2011 From the US Patent and Trademark Office Re. U.S. Appl. No. 12/656,048.
Response Dated Feb. 18, 2011 to Examination Report Dated Sep. 20, 2010 From the Instituto Mexicano der la Propriedad Industrial Re.. Application No. MX/a/2007/015511 and Its Translation Into English.
Response Dated Sep. 7, 2011 to Official Action of Jul. 12, 2011 From the US Patent and Trademark Office Re. U.S. Appl. No. 11/921,578.
Translation of Final Notice of the Reason for Rejection Dated Aug. 31, 2011 From the Korean Intellectual Property Office Re. Application No. 2010-7016372.
Translation of Notice of Reason for Rejection Dated Nov. 2, 2010 From the Japanese Patent Office Re. Application No. 2007-504560.
Translation of Notice of the Reason for Rejection Dated Oct. 28, 2010 From the Korean Itellectual property Office Re. Application No. 2010-7016372.
Communication Relating to the Results of the Partial International Search Dated May 10, 2007 From the International Searching Authority Re.: Application No. PCT/IL2006/000666.
International Preliminary Report on Patentability Dated Dec. 3, 2007 From the International Preliminary Examining Authority Re.: Application No. PCT/IL2006/000666.
International Preliminary Report on Patentability Dated Oct. 17, 2007 From the International Preliminary Examining Authority Re.: Application No. PCT/IL2006/000666.
Official Action Dated Feb. 16, 2010 From the US Patent and Trademark Office Re.: U.S. Appl. No. 12/585,021.
Response Dated Jan. 13, 2010 to Notice for Reason for Rejection of Oct. 20, 2009 From the Japanese Patent Office Re.: Application No. 2003-530202.

Response Dated Jan. 13, 2010 to Office Action of Jul. 17, 2009 From the State Intellectual Property Office of the People's Republic of China Re.: Application No. 200580017025.1.
Response Dated Dec. 30, 2009 to Office Action of Aug. 31, 2009 From the Israel Patent Office Re.: Application No. 161083.
Chan et al. "Phenothiazine Inhibitors of Trypanothione Reductase as Potential Antitrypanosomal and Antileishmanial Drugs", Journal of medicinal Chmeistry, 41(2): 148-156, 1998.
Gil-Ad et al. "Novel Anti-Psychotics That Display GABAergic Acitivity and Decreased Extrapyramidal Side Effects, for the Treatment of Schizophrenia and Related Psychiatric Disorders", Neural Plasticity, 10(3): 200, 2003. Abstract.
Ware et al. "An Automated Approach to Salt Selection for New Unique Trazodone Salts", Pharmaceutical Research, 21(1): 177-184, 2004. Abstract.
Wilson et al. "Central Nervous System Depressant", Wilson and Gisvold's Textbook of Organic Medicinal and Pharmaceutical Chemistry, 8th Ed., p. 362-371, 1982.
Response Dated Aug. 22, 2011 to Office Action of Jun. 24, 2011 From the State Intellectual Property Office of the People's Republic of China Re. Application No. 200780033294.6.
Official Action Dated Aug. 25, 2011 From the US Patent and Trademark Office Re. U.S. Appl. No. 12/655,048.
Requisition by the Examiner Dated Aug. 2, 2011 From the Canadian Intellectual Property Office Re. Application No. 2,560,905.
Official Action Dated Dec. 14, 2010 From the US Patent and Trademark Office Re.: U.S. Appl. No. 12/585,021.
Response Dated Dec. 23, 2010 to Office Action of Aug. 23, 2010 From the Israel Patent Office Re. Application No. 203058.
Communication Relating to the Results of the Partial International Search Dated Nov. 27, 2007 From the International Searching Authority Re.: Application No. PCT/IL2007/000903.
International Preliminary Report on Patentability Dated Jan. 29, 2009 From the International Bureau of WIPO Re.: Application No. PCT/IL2007/000902.
International Preliminary Report on Patentability Dated Jan. 29, 2009 From the International Bureau of WIPO Re.: Application No. PCT/IL2007/000903.
Office Action Dated Feb. 15, 2009 From the Israeli Patent Office Re.: Application No. 161083.
Official Action Dated Jun. 19, 2008 From the US Patent and Trademark Office Re.: U.S. Appl. No. 11/636,599.
Official Action Dated Oct. 31, 2008 From the US Patent and Trademark Office Re.: U.S. Appl. No. 12/005,342.
Communication Relating to the Results of the Partial International Search Dated Jun. 13, 2006 From the International Searching Authority Re.: Application No. PCT/IL2005/000341.
Communication Relating to the Results of the Partial International Search Dated Nov. 20, 2007 From the International Searching Authority Re.: Application No. PCT/IL2007/000902.
International Preliminary Report on Patentability Dated Oct. 12, 2006 From the International Bureau of WIPO Re.: Application No. PCT/IL2005/000341.
International Search Report Dated Jun. 25, 2009 From the International Searching Authority Re.: Application No. PCT/IL2009/000158.
Invitation to Pay Additional Fees Dated Jun. 13, 2006 From the International Searching Authority Re.: Application No. PCT/IL2005/000341.
Invitation to Pay Additional Fees Dated Nov. 20, 2007 From the International Searching Authority Re.: Application No. PCT/IL2007/000902.
Invitation to Pay Additional Fees Dated Nov. 27, 2007 From the International Searching Authority Re.: Application No. PCT/IL2007/000903.
Notice of Allowance Dated Jul. 10, 2009 From the US Patent and Trademark Office Re.: U.S. Appl. No. 11/636,599.
Official Action Dated Feb. 1, 2007 From the US Patent and Trademark Office Re.: U.S. Appl. No. 10/808,541.
Official Action Dated Jul. 25, 2006 From the US Patent and Trademark Office Re.: U.S. Appl. No. 10/808,541.
Response Dated Nov. 23, 2009 to Office Action of Jul. 23, 2009 From the Israel Patent Office Re.: Application No. 199877.

Translation of Notice for Reason for Rejection Dated Oct. 20, 2009 From the Japanese Patent Office Re.: Application No. 2003-530202.
Translation of Notice of the Reason for Rejection Dated Aug. 26, 2009 From the Korean Intellectual Property Office Re.: Application No. 2004-7004581.
Translation of Office Action Dated Jul. 17, 2009 From the State Intellectual Property Office of the People's Republic of China Re.: Application No. 200580017025.1.
Written Opinion Dated Jun. 25, 2009 From the International Searching Authority Re.: Application No. PCT/IL2009/000158.
Dutta et al. "Existing Dopaminergic Therapies for Parkinson's Disease", Expert Opinion on Therapeutic Patents, XP002531574, 16: 1613-1625, 2006. § [04.1], Fig. 1.
Florence et al. "Prolongation of the Action of Intramuscular Formulations of Phenothiazines", Optimization of Drug Delivery, 17th Alfred Benzon Symposium, Mungsgaard, Copenhagen, p. 93-111, 1982.
Merck "Schizophrenia", the Merck Manuals, Section Psychiatric Disorders, 17th Ed.: 1569-1575, Dec. 10, 1999. Japanese Version and Its Translation Into English. p. 1572, Right Col., Line 15—p. 1573, Left Col., Line 11, p. 1574, Table 193-1.
Napolitano et al. "New Directions in Parkinson's Research and Treatment", Expert Opinion on Therapeutic Patents, XP002531575, 8: 1251-1268, 1998. Fig.4.
Advisory Action Before the Filing of an Appeal Brief Dated Jan. 10, 2012 From the US Patent and Trademark Office Re. U.S. Appl. No. 12/655,048.
Examination Report Dated Dec. 5, 2011 From the Instituto Mexicano de la Propriedad Industrial Re. Application No. MX/a/2009/000641 and Its Summary in English.
Examiner's Report Dated Jan. 24, 2012 From the Australian Government, IP Australia Re. Application No. 2006256369.
Examination Report Dated Jan. 19, 2012 From the Instituto Mexicano de la Propriedad Industrial Re. Application No. MX/a/2007/015511 and Its Translation Into English.
International Search Report and the Written Opinion Dated Feb. 8, 2012 From the International Searching Authority Re.: Application No. PCT/IL2011/000752.
Official Action Dated Feb. 2, 2012 From the US Patent and Trademark Office Re. U.S. Appl. No. 12/655,048.
Summons to Attend Oral Proceedings Pursuant to Rule 115(1) EPC Dated Jan. 26, 2012 From the European Patent Office Re. Application No. 06756205.8.
Rephaeli et al. "Gamm-Aminobutyric Acid Amides of Nortriptyline and Fluoxetine Display Improved Pain Suppressing Activity", Journal of Medicinal Chemistry, XP002668033, 52(9): 3010-3017, 2009. Scheme 1, Experimental Section.
Advisory Action Before the Filing of an Appeal Brief Dated Oct. 25, 2011 From the US Patent and Trademark Office Re. U.S. Appl. No. 12/764,124.
Examiner's Report Dated Oct. 7, 2011 From the Australian Government, IP Australia Re. Application No. 2007274583.
Translation of Notice of Reason for Rejection Dated 30, Sep. 2011 From the Japanese Patent Office Re. Application No. 2007-504560.
Response Dated Oct. 19, 2011 to Official Action Dated Aug. 5, 2011 From the US Patent and Trademark Office Re. U.S. Appl. No. 12/764,124.
Response Dated Oct. 23, 2011 to Office Action Dated May 17, 2011 From the Israel Patent Office Re.: Application No. 187892.
Official Action Dated Nov. 1, 2011 From the US Patent and Trademark Office Re. U.S. Appl. No. 11/921,578.

Bastin et al. "Salt Selection and Optimisation Procedures for Pharmaceutical New Chemical Entities", Organic Process Research & Development, 4: 427-435, 2000.
International Search Report and the Written Opinion Dated Dec. 1, 2011 From the International Searching Authority Re. Application No. PCT/IB2011/000915.
Notice of Allowance Dated Dec. 1, 2011 From the US Patent and Trademark Office Re. U.S. Appl. No. 12/764,124.
Official Action Dated Nov. 22, 2011 From the US Patent and Trademark Office Re. U.S. Appl. No. 12/309,361.
Translation of Office Action Dated Jan. 5, 2012 From the State Intellectual Property Office of the People's Republic of China Re. Application No. 200810190781.X.
Communication Under Rule 71(3) EPC Dated Feb. 20, 2012 From the European Patent Office Re. Application No. 09711260.1.
Notice of Allowance Dated Feb. 23, 2012 From the US Patent and Trademark Office Re. U.S. Appl. No. 12/867,055.
Translation of Office Action Dated Feb. 23, 2012 From the State Intellectual Property Office of the People's Republic of China Re. Application No. 200780033294.6.
Translation of Office Action Dated Jan. 30, 2012 From the State Intellectual Property Office of the People's Republic of China Re.: Application No. 200680029378.8.
Communication Under Rule 71(3) EPC Dated Sep. 21, 2011 From the European Patent Office Re. Application No. 02772790.8.
Response Dated Oct. 3, 2011 to Office Action of Jun. 6, 2010 From the Israeli Patent Office Re.: Application No. 161083.
Requisition by the Examiner Dated Aug. 2, 2011 From the Canadian Intellectual Property Office Re. Application No. 2,461,663.
Official Action Dated Jan. 31, 2012 From the US Patent and Trademark Office Re. U.S. Appl. No. 12/309,361.
Official Action Dated Jan. 31, 2012 From the US Patent and Trademark Office Re. U.S. Appl. No. 13/034,453.
Morissette et al. "High-Througput Crystallization: Polymorphs, Salts, Co-Crystals and Solvates of Pharmaceutical Solids", Advanced Drug Delivery Reviews, 56: 275-300, 2004.
Communication Under Rule 71(3) EPC Dated Nov. 28, 2011 From the European Patent Office Re. Application No. 07789958.1.
Response Dated Dec. 14, 2011 to Notice of Reason for Rejection of Sep. 30, 2011 From the Japanese Patent Office Re. Application No. 2007-504560.
Response Dated Dec. 15, 2011 to Examiner's Report of Oct. 21, 2010 From the Australian Government, IP Australia Re. Application No. 2006256369.
Translation of Notice of Reason for Rejection Dated Nov. 29, 2011 From the Japanese Patent Office Re. Application No. 2008-515378.
Communication Pursuant to Article 94(3) EPC Dated Jan. 26, 2012 From the European Patent Office Re. Application No. 10182948.9.
Response Dated Nov. 24, 2011 to Official Action of Aug. 25, 2011 From the US Patent and Trademark Office Re. U.S. Appl. No. 12/655,048.
Supplemental After Final Amendment Dated Nov. 17, 2011 in Response to Official Action Dated Aug. 5, 2011 From the US Patent and Trademark Office Re. U.S. Appl. No. 12/764,124.
Translation of Office Action Dated Nov. 3, 2011 From the State Intellectual Property Office of the People's Republic of China Re.: Application No. 200580017025.1.
Office Action Dated Dec. 12, 2011 From the Israel Patent Office Re.: Application No. 187892 and Its Translation Into English.

* cited by examiner

CONJUGATES COMPRISING A GABA- OR GLYCINE COMPOUND, PHARMACEUTICAL COMPOSITIONS AND COMBINATIONS THEREOF AND THEIR USE IN TREATING CNS DISORDERS

RELATED APPLICATIONS

This Application is a National Phase of PCT Patent Application No. PCT/IL2007/000902 having International filing date of Jul. 17, 2007, which claims the benefit of U.S. Provisional Patent Application No. 60/831,195 filed on Jul. 17, 2006, and 60/831,192, filed on Jul. 17, 2006. The contents of the above Applications are all incorporated herein by reference.

FIELD AND BACKGROUND OF THE INVENTION

The present invention relates to the field of pharmacology and more particularly, to novel conjugates, pharmaceutical compositions including same and to uses thereof for treating CNS-associated diseases and disorders.

γ-Aminobutyric acid (GABA) is one of the major inhibitory transmitters in the central nervous system of mammals. GABA is not transported efficiently into the brain from the bloodstream because of poor transport properties that prevent passage through the blood-brain barrier. Consequently, brain cells synthesize virtually all of the GABA found in the brain (by decarboxylation of glutamic acid with pyridoxal phosphate).

GABA regulates neuronal excitability through binding to specific membrane proteins (i.e., GABA receptors), which results in opening of an ion channel. The entry of chloride ion through the ion channel leads to hyperpolarization of the recipient cell, which consequently prevents transmission of nerve impulses to other cells. Low levels of GABA have been observed in individuals suffering from epileptic seizures, motion disorders (e.g., Parkinson's disease, Multiple Sclerosis, action tremors, tardive dyskinesia), panic, anxiety, depression, alcoholism and manic behavior. Administering GABA to the brain is therefore expected to improve symptoms of these diseases and disorders.

Unfortunately, the clinical use of GABA for treating CNS-associated diseases or disorders is presently limited since the GABA molecule includes hydrophilic functional groups (e.g., a free carboxylic acid group and a free amino group) and therefore does not readily cross the blood brain barrier (BBB).

Recent studies on extrapyramidal symptoms suggest that GABA may reduce side effects of psychotropic drugs, and particularly side effects induced by neuroleptics. Psychotropic drugs are pharmacological agents which act mainly in the central nervous system (CNS) by modulating neuronal signals transduction. Unfortunately, the administration of psychotropic drugs is often associated with adverse side effects which severely limit their use. A comprehensive list of such side effects can be found, for example, in "The Merck Manual of Medical Information" (Merck & Co. Inc.).

Furthermore, previous studies have suggested that GABA can interfere with other brain neurotransmitters and, in particular, with the dopamine system. Thus, it was found that GABA can antagonize the neuroleptic-induced increase of dopamine receptors sensitivity and is therefore capable of improving neuroleptic-induced dyskinesia (Lloyd et al., Pharmacol. Biochem. Behav. 18: 957-66, 1983).

In addition, it was found that some known direct GABA agonists (e.g., muscimol and SL 76002) cause a biphasic effect on haloperidol-induced catalepsy, such that while low doses of the agonist inhibit the stereotypic catalepsy behavior, high doses of the agonist potentiate the haloperidol-induced catalepsy. Other studies have reported that GABA agonists further induce anti-convulsive activity (Capasso et al., Eur. Neuropsychopharmacol. 7: 57-63, 1997).

Thus, while GABA, as well as other GABA agonists, can serve as highly potent agents for treating, interfering or otherwise beneficially affecting CNS-associated conditions (e.g., by reducing side effects induced by psychotropic drugs), the use of these compounds is limited by their low permeability through the blood brain barrier and hence by poor delivery of such compounds into the brain.

A series of conjugates of psychotropic drugs and GABA and their use in the treatment of psychotic and/or proliferative diseases and disorders are described in detail in International Patent Applications published as WO 03/026563 and WO 2005/092392 and in U.S. Patent Application No. 20040242570, which are all incorporated by reference as if fully set forth herein.

Glycine is another important inhibitory transmitter in the central nervous system of mammals. Similarly to GABA, glycine is not transported efficiently into the brain from the bloodstream since the glycine molecule includes hydrophilic functional groups (a free carboxylic acid group and a free amino group) and therefore does not readily cross the blood-brain barrier (BBB).

Glycine regulates neuronal excitability through binding to strychnine-sensitive and strychnine-insensitive glycine binding sites. The strychnine-insensitive glycine binding site is located on the N-methyl-D-aspartate (NMDA) receptor complex. Glycine binds with high affinity to this site, leading to opening of an ion channel. The entry of chloride ion through the ion channel leads to hyperpolarization of the recipient cell, which consequently prevents transmission of nerve impulses to other cells.

Despite its poor capacity to cross the BBB, glycine in high doses may be beneficial in the management of CNS diseases and disorders.

Accordingly, high-dose glycine supplementation has been shown to improve the "negative symptoms" of schizophrenia (such as "flat" emotional expression, depression, poverty of speech, apathy, and social withdrawal). Glycine also appears to boost the efficacy, and reduce the side-effects, of schizophrenia medications (Heresco-Levy et al., Arch Gen Psychiatry. 56:29-36, 1999; Coyle and Tsai, Psychopharmacology 174:32-38, 2004; Shoham et al., Brain Res. 1004:142-147, 2004).

Glycine has also been shown to reduce convulsive seizures per se (de Kooning et al., Ann. Neurol 44:261-265, 1998; Toth and Lajtha, Neurochem Res. 9:1711-1718, 1984) or to potentiate the efficiency of anti-convulsive drugs (Liu et al., Eur J Pharmacol. 182:109-15, 1990).

In addition, glycine supplementation has been shown to improve learning and cognition in healthy human adults (File et al., J. Clin. Psychopharmacol 19:506-512, 1999).

U.S. Pat. No. 4,639,468 describes the compound 2-N-pentylaminoacetamide (milacemide) which crosses the BBB and acts as a glycine prodrug to deliver glycine to the brain. Milacemide is metabolized by monoamine oxidase B (MAO-B) to glycinamide which in turn is converted to glycine.

SUMMARY OF THE INVENTION

The present invention provides a novel approach for delivering a GABA compound and/or a glycine compound into brain tissues, to thereby treat CNS-associated diseases or disorders, reduce adverse side effects induced by CNS-acting agents (e.g., psychotropic drugs) and/or enhance the therapeutic activity of CNS-acting agents (e.g., psychotropic drugs).

This approach is based on coupling a GABA compound, as defined herein, or a glycine compound, as defined herein, to a molecule such as an analgesic, so as to provide a novel conjugate which would penetrate the BBB and thus would release both the GABA compound or the glycine compound and an analgesic in brain tissues. Such a conjugate can exhibit a therapeutic activity by e.g., inhibiting neurotransmitters in the GABA system and/or by exerting an analgesic activity in the central nervous system, or can be combined with another CNS-acting agent, so as to provide an added therapeutic value, to enhance the therapeutic activity of the agent, and/or to reduce side effects induced by the agent.

Thus, according to one aspect of the present invention there is provided a conjugate comprising a first moiety being covalently linked to a second moiety, wherein the first moiety is a γ-aminobutyric acid (GABA) compound or a glycine compound and the second moiety is an analgesic drug.

According to further features in embodiments of the invention described below, the analgesic drug is a non-steroidal anti-inflammatory drug.

According to still further features in the described embodiments the analgesic drug is a CNS-acting analgesic drug.

According to still further features in the described embodiments the CNS-acting analgesic drug is acting upon the opioid response system.

According to still further features in the described embodiments the CNS-acting analgesic drug is incapable of acting upon the opioid response system.

According to still further features in the described embodiments the CNS-acting analgesic drug is acetaminophen.

According to still further features in the described embodiments the first and second moieties are linked therebetween via a covalent bond selected from the group consisting of a carboxylic ester bond, an alkyloxy carboxylic ester bond, an amide bond, an imine bond and a thioester bond.

According to still further features in the described embodiments the covalent bond is a carboxylic ester bond.

According to still further features in the described embodiments the first moiety is GABA, the second moiety is acetaminophen, and further, the GABA and the acetaminophen are linked via a carboxylic ester bond.

According to still further features in the described embodiments the first moiety is glycine, the second moiety is acetaminophen, and further, the glycine and the acetaminophen are linked via a carboxylic ester bond.

According to still further features in the described embodiments the first moiety is selected from the group consisting of a radiolabeled γ-aminobutyric acid (GABA) compound (e.g., a radiolabeled GABA) and a radiolabeled glycine compound (e.g., a radiolabeled glycine).

In embodiments of the present invention, the following compounds are provided:

An acetaminophen-GABA conjugate having the formula:

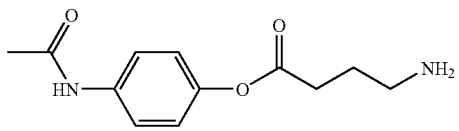

An acetaminophen-glycine conjugate having the formula:

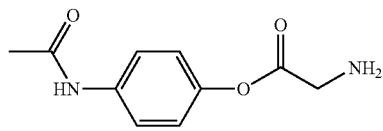

According to another aspect of the present invention there is provided a pharmaceutical composition comprising, as an active ingredient, any of the conjugates described herein and a pharmaceutically acceptable carrier.

According to further features in embodiments of the invention described below, the pharmaceutical composition further comprising a CNS-acting agent.

According to still further features in the described embodiments the analgesic drug is a CNS-acting analgesic drug that is incapable of acting upon the opioid response system.

According to further features in embodiments of the invention described below, the CNS-acting agent is a psychotropic drug.

According to still further features in the described embodiments, the psychotropic drug is selected from the group consisting of an anti-psychotic drug, an anxiolytic drug, an antidepressant drug, an anti-convulsive drug, an anti-parkinsonian drug, an acetylcholine esterase inhibitor, a MAO inhibitor, a selective serotonin reuptake inhibitor (SSRI) and a selective noradrenalin replace inhibitor (SNRI).

According to still further features in the described embodiments, a molar ratio of the conjugate and the CNS-acting agent ranges from about 1:100 to about 100:1, preferably from about 1:10 to about 10:1, and more preferably is about 1:1.

According to still further features in the described embodiments, the pharmaceutical composition is packaged in a packaging material and identified in print, in or on the packaging material, for use in the treatment of a CNS-associated disease or disorder, for reducing side effects induced by a psychotropic drug and/or for enhancing the therapeutic efficacy of a psychotropic drug.

According to yet another aspect of the present invention there is provided an article-of-manufacturing comprising the pharmaceutical composition, as described herein, being packaged in a packaging material and identified in print, on or in the packaging material, for use in the treatment of a CNS-associated disease or disorder, for reducing side effects induced by a CNS-acting agent (e.g., a psychotropic drug) and/or for enhancing the therapeutic efficacy of a CNS-acting agent (e.g., a psychotropic drug).

According to further features in embodiments of the invention described below, the conjugate and the CNS-acting agent are jointly contained within a single object.

According to still further features in the described embodiments, the single object is a tablet or a capsule.

According to still further features in the described embodiments, the conjugate and the CNS-acting agent are separately contained within different objects.

According to still further features in the described embodiments, each of the objects is independently a tablet or a capsule.

According to still further features in the described embodiments the CNS-associated disease or disorder is selected from the group consisting of a pain disorder, an anxiety disorder, a depression, a dissociative disorder, a personality disorder, a cognitive disorder, a mood disorder, an affective disorder, a neurodegenerative disease or disorder, a convulsive disorder, Parkinson's disease, Alzheimer's disease and epilepsy.

According to still another aspect of the present invention there is provided use of any the conjugates described herein in the preparation of a medicament.

According to further features in embodiments of the invention described below, the medicament is for treating a CNS-associated disease or disorder.

According to still further features in the described embodiments, the medicament is for reducing a side effect induced by a CNS-acting agent.

According to still further features in the described embodiments, the medicament is for enhancing a therapeutic activity of a CNS-acting agent.

According to an additional aspect of the present invention there is provided a method of treating a CNS-associated disease or disorder, the method comprising administering to a subject in need thereof a therapeutically effective amount of the conjugate described herein, thereby treating the CNS-associated disease or disorder, as described herein.

According to further features in embodiments of the invention described below, the conjugate forms a part of a pharmaceutical composition which further comprises a pharmaceutically acceptable carrier.

According to yet an additional aspect of the present invention there is provided a method of reducing an adverse side effect induced by a CNS-acting agent, the method comprising administering to a subject in need thereof, in combination with the CNS-acting agent, a therapeutically effective amount of the conjugate described herein, thereby reducing the adverse side effect induced by the CNS-acting agent.

According to further features in embodiments of the invention described below, the conjugate forms a part of a pharmaceutical composition which further comprises a pharmaceutically acceptable carrier.

According to still further features in the described embodiments, the pharmaceutical composition further comprises the CNS-acting agent.

According to still further features in the described embodiments, the conjugate is administered prior to, concomitant with or subsequent to administering the CNS-acting agent.

According to still further features in the described embodiments, the CNS-acting agent is a psychotropic drug.

According to still further features in the described embodiments, the adverse side effect is selected from the group consisting of rigidity, tremor, bradykinesia, bradyphrenia, tardive dyskinesia, catalepsy, acute dystonic reactions and akathasia.

According to still an additional aspect of the present invention there is provided a method of enhancing the therapeutic activity of a CNS-acting agent, the method comprising administering to a subject in need thereof, in combination with the CNS-acting agent, a therapeutically effective amount of the conjugate described therein, thereby enhancing the therapeutic activity of the CNS-acting agent.

According to further features in embodiments of the invention described below, the conjugate forms a part of a pharmaceutical composition that further comprises a pharmaceutically acceptable carrier.

According to still further features in the described embodiments, the pharmaceutical composition further comprises a CNS-acting agent.

According to still further features in the described embodiments, the conjugate is administered prior to, concomitant with or subsequent to administering the CNS-acting agent.

According to still further features in the described embodiments, the CNS-acting agent is a psychotropic drug.

According to a further aspect of the present invention there is provided a method of treating a CNS-associated disease or disorder, as described herein, the method comprising administering to a subject in need thereof a therapeutically effective amount of a CNS-acting agent and a therapeutically effective amount of a conjugate as described herein.

According to further features in embodiments of the invention described below, the conjugate is administered prior to, concomitant with or subsequent to administering the CNS-acting agent.

According to still further features in the described embodiments, the CNS-acting agent is a psychotropic drug.

According to still a further aspect of the present invention there is provided a method of determining a concentration of a conjugate which comprises a first moiety being covalently linked to a second moiety, wherein the first moiety is a γ-aminobutyric acid (GABA) compound or a glycine compound and the second moiety is an analgesic drug and/or a concentration of the first moiety upon being released from the conjugate, in a tissue of a subject, the method comprising:

administering to the subject a pre-determined amount of a radiolabeled conjugate which comprises a radiolabeled first moiety being covalently linked to a second moiety, wherein the first moiety is a radiolabeled γ-aminobutyric acid (GABA) compound or a radiolabeled glycine compound and the second moiety is an analgesic drug; and determining a concentration of the radiolabeled conjugate and/or the radiolabeled first moiety in the tissue.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

As used herein, the singular form "a," "an," and "the" include plural references unless the context clearly dictates otherwise. For example, the term "a compound" or "at least one compound" may include a plurality of compounds, including mixtures thereof.

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "about" refers to ±10%.

The term "comprising" means that other steps and ingredients that do not affect the final result can be added. This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

The term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

The term "active ingredient" refers to a pharmaceutical agent including any natural or synthetic chemical substance that subsequent to its application has, at the very least, at least one desired pharmaceutical or therapeutic effect.

DESCRIPTION OF THE PREFERRED EMBODIMENTS

The present invention is of conjugates capable of carrying a GABA compound or a glycine compound across the blood-brain barrier (BBB) and which can be used in the treatment of CNS-associated diseases or disorders, either alone or in combination with a CNS-acting agent. Specifically, the present invention is of conjugates of a GABA compound or a glycine compound and an analgesic drug, processes of preparing these conjugates, pharmaceutical compositions containing these conjugates and uses thereof for treating CNS-associated diseases and disorders, for improving efficiency of CNS-acting agents and/or for reducing adverse side effects of CNS-acting agents.

The principles and operation of the present invention may be better understood with reference to the accompanying descriptions.

Before explaining at least one embodiment of the invention in detail, it is to be understood that the invention is not limited in its application to the details of construction and the arrangement of the components set forth in the following description. The invention is capable of other embodiments or of being practiced or carried out in various ways. Also, it is to be understood that the phraseology and terminology employed herein is for the purpose of description and should not be regarded as limiting.

The present inventors have designed and successfully prepared and practiced a novel methodology which allows the administration GABA or any GABA compound, as defined herein, by conjugating the GABA compound to a moiety that serves as a carrier of the GABA compound, such that the resulting conjugate would be capable of delivering the GABA compound to the brain tissues.

In the conjugates described herein, GABA or a GABA compound is attached to a carrier molecule, which is selected so as to enable the conjugate to cross the BBB and release GABA (or a GABA compound) in the brain tissues (and thus delivering the GABA compound to brain tissues). These conjugates can be utilized, either alone, or in combination with another therapy (e.g., psychotropic drugs), in treating, interfering or otherwise beneficially affecting various CNS-associated conditions.

Utilizing such conjugates, in combination with a psychotropic drug, enables (i) to use in such a combined therapy a variety of psychotropic drugs, regardless of their chemical compatibility in forming covalent bonds with GABA (or any GABA compound); (ii) to practice in such a combined therapy versatile molar ratios of the psychotropic drug and the conjugate, so as to achieve an optimal efficacy of the combined therapy; and (iii) to practice a pre-determined, distinctly-timed administration of the components so as to achieve an optimal efficacy of the combined therapy.

The novel methodology described herein can be further utilized to provide conjugates of glycine (or a glycine compound) and a moiety that serves as a carrier thereof, which are capable of delivering the glycine compound to the brain tissues, and thus can be utilized in treating CNS diseases and disorders.

The above methodology has been practiced by conjugating a GABA compound or a glycine compound to an analgesic. The analgesic serves as an efficient carrier molecule for delivering a GABA compound or a glycine compound to the brain.

As is well-known in the art, analgesics (otherwise known as pain killers) is a collective term used to describe members in the diverse group of drugs used to relieve pain. Analgesic drugs act via various pathways on the peripheral and central nervous system. Analgesics can be divided into non-narcotic drugs, such as acetaminophen (paracetamol) and non-steroidal anti-inflammatory drugs (e.g., aspirin, naproxen, etc.) and narcotic drugs such as morphine and synthetic drugs with narcotic properties such as tramadol.

Preferred analgesics are CNS-acting analgesics, which are known to be capable of exerting therapeutic activity (e.g., analgesic and/or antipyretic) is in the CNS.

An example of a CNS-acting analgesic is acetaminophen, which is known to penetrate the BBB. Thus, an exemplary conjugate according to the present embodiments is an ester-linked acetaminophen-GABA conjugate. By conjugating GABA to acetaminophen via an ester bond, the hydrophilic nature of GABA is reduced due to the participation of the free carboxylic group in GABA in the ester bond. Such a novel conjugate can be freely administered alone, so as to exert therapeutic activities associated with GABA, or in combination with existing psychotropic drugs, so as to exert GABA-associated therapeutic activity, to enhance the therapeutic activity of the psychotropic drugs and/or to reduce adverse side effects induced by the psychotropic drugs.

Another exemplary conjugate according to the present embodiments is an ester-linked acetaminophen-glycine conjugate.

Thus, according to one aspect of the present invention, there is provided a conjugate which comprises a first moiety and a second moiety being covalently linked therebetween, whereby the first moiety is a γ-aminobutyric acid (GABA) compound or a glycine compound and the second moiety is an analgesic drug.

According to one embodiment of this aspect of the present invention, the first moiety and the second moiety, as well as the covalent bond linking therebetween, are selected such that the conjugate is incapable of releasing a formaldehyde molecule and/or a formaldehyde analog molecule upon cleavage.

As used herein, the term "moiety" describes a compound that has a pharmacological activity. When described in the context of the conjugates presented herein, this term is understood to include a major portion of a molecule which is covalently linked to another molecule, preferably while maintaining the activity of the molecule.

The term "derivative" describes a compound which has been subjected to a chemical modification while maintaining its main structural features. Such chemical modifications can include, for example, replacement of one or more substituents and/or one or more functional moieties, oxidation, reduction, and the like.

As used herein, the phrase "analgesic drug", which is also referred to herein interchangeably as "analgesic", encompasses any drug which is capable of relieving pain in a subject, as is detailed hereinabove. Excluded from the scope of the present invention, however, are anti-depressants, anti-convulsants and anti-anxiety drugs, as well as other psychotropic drugs which, although typically not considered as analgesics, may exhibit an analgesic activity and hence may be used to treat a neuropathic pain.

Herein throughout, the phrase "analgesic drug" or "analgesic" is used to describe both the analgesic drug and any derivative thereof, as this term is defined herein, unless otherwise indicated.

An analgesic drug, according to the present embodiments, can be a non-steroidal anti-inflammatory (NSAID) drug. NSAIDs act by inhibiting cyclooxygenase, to thereby decrease prostaglandin production and as a result affect pain and inflammation. Representative examples of NSAIDs include, but are not limited to, bromfenac, diclofenac, diflunizal, etodolac, mefenamic, meloxicam, oxyphenbutazone, piroxicam, celecoxib, valdecoxib or any derivative thereof.

Preferably, the analgesic drug, according to the present embodiments, is a CNS-acting analgesic drug.

The phrase "CNS-acting analgesic drug" (also referred to herein interchangeably as "CNS-acting analgesic", as used herein, describes an analgesic drug that is capable of acting on the central nervous system.

According to one embodiment, a CNS-acting analgesic drug or a derivative thereof, according to the present embodiments, is selected incapable of exerting a non-analgesic and/or non-antipyretic psychotropic activity (e.g., selected incapable of exerting anti-psychotic, anti-depressants, anti-convulsants, or anti-anxiety activities).

As is well-known in the art, many CNS-acting analgesics typically act upon the opioid response system. As used herein, the phrase "CNS-acting agent acting upon the opioid response system" refers to a drug that acts by binding to an opioid receptor in the central nervous system. These drugs are commonly referred to as opioids and are considered as narcotic analgesics. Representative examples of such CNS-acting analgesic drugs include, but are not limited to, morphine, codeine, hydrocodone, hydromorphone, levorphanol, oxycodone, oxymorphone, naloxone, naltrexone, alfentanil, buprenorphine, butorphanol, dezocine, fentanyl, meperidine, methadone, nalbuphine, pentazocine, propoxyphene, sufentanil, tramadol or any derivative thereof.

Some CNS-acting analgesics, however, are not acting upon the opioid response system and are typically considered as non-narcotic analgesics. Thus, in one embodiment, the CNS-acting analgesic in the conjugate is not acting upon the opioid response system. Exemplary such non-opioid CNS-acting analgesic drugs include, but are not limited to, acetaminophen and derivatives thereof.

Acetaminophen, also known as N-acetyl-para-aminophenol (APAP) or paracetamol, is a widely used analgesic drug. Acetaminophen acts in the CNS and is characterized by highly efficient anti-pyretic activity. It is not addictive and has an excellent safety profile. The maximum daily dose of acetaminophen allowed in adults without prescription is 4,000 mg.

As used herein throughout, the phrase "a GABA compound" encompasses GABA itself, any derivative thereof as well as GABA agonists and any derivatives thereof, as defined herein.

As used herein, the phrase "GABA agonist" encompasses compounds that are capable of activating the GABA system in the brain, either directly or indirectly, including compounds that directly bind the GABA receptor or to any other receptor that affects the GABA system, and are therefore pharmacologically related to GABA.

GABA agonists, according to the present embodiments, include any GABA agonist which can be covalently coupled to an analgesic drug or a derivative thereof either as is or upon derivatization (so as to produce a derivative thereof).

The phrase "a glycine compound", as used herein, encompasses glycine, as well as derivatives thereof, as defined herein.

Any of the novel conjugates presented herein therefore comprises a GABA compound or a glycine compound (being the first moiety), as detailed hereinabove, and an analgesic drug or a derivative thereof (being the second moiety), as detailed hereinabove, whereby these moieties are covalently attached to one another.

In one embodiment, the first moiety is GABA.

In another embodiment, the first moiety is glycine.

In other embodiments of the present invention, the first and second are attached to one another via a covalent bond that is selected or designed capable of dissociating following crossing of the blood-brain barrier.

Thus, the covalent bond linking the first and the second moieties is preferably selected or designed such that (i) it is not susceptible to dissociation (e.g., by enzymatic reactions) in the periphery and hence the conjugate remains substantially intact before crossing the BBB; and (ii) it is susceptible to dissociation in brain tissues (e.g., by brain derived enzymes), and hence the conjugate dissociates following crossing the BBB.

A suitable bond can be, for example, a carboxylic ester bond, an oxyalkyl carboxylic ester bond, an amide bond, a thioester bond, a glycoside bond, a carbonate bond, a carbamate bond, a thiocarbamate bond, an imine bond, a urea bond or a thiourea bond.

As used herein, a "carboxylic ester bond" describes an "—O—C(=O)-" bond.

As used herein, an "oxyalkyl carboxylic ester bond" describes an "O—R—O—C(=O)-" bond, where R is an alkylene, as defined hereinabove. Preferably R is any alkylene other than methylene.

An "amide bond" describes a "—NR'—C(=O)—" bond, where R' is hydrogen, alkyl, cycloalkyl or aryl, as defined herein.

A "thioester bond" describes a "—SR'—C(=O)—" bond, where R' is as defined herein.

A "glycoside bond" describes a —R—O—R— bond, where each R can independently be alkylene, such as methylene, or absent.

A "carbonate bond" describes a —C(=O)— bond.

A "carbamate bond" describes a —O—C(=O)—NR'— bond, where R' is as defined herein.

A "thiocarbamate bond" describes a O—C(=S)—NR'— bond, where R' is as defined herein.

A "urea bond" describes a —NR"C(=O)—NR'— bond, where R' is as defined herein and R" is as defined herein for R'.

A "thiourea bond" describes a —NR'—C(=S)—NR" bond, with R' and R" as defined herein.

As used herein, the term "imine bond" describes a —C=NH— bond. An imine bond is also known in the art as a "Schiff base".

As used herein, the term "alkyl" describes a saturated aliphatic hydrocarbon chain including straight chain and branched chain groups. Preferably, the alkyl group has 1 to 20 carbon atoms. Whenever a numerical range, e.g., "1-20", is stated herein, it means that the group, in this case the alkyl group, may contain 1 carbon atom, 2 carbon atoms, 3 carbon atoms, etc., up to and including 20 carbon atoms. More preferably, the alkyl is a medium size alkyl having 1 to 10 carbon atoms. Most preferably, the alkyl has 1 to 5 carbon atoms.

The term "alkylene" describes an alkyl group that is linked to two other groups. Thus, the term ethylene, for example, describes a —CH$_2$CH$_2$— group.

As used herein, the term "cycloalkyl" describes an all-carbon monocyclic or fused ring (i.e., rings which share an adjacent pair of carbon atoms) group wherein one of more of the rings does not have a completely conjugated pi-electron system. Examples, without limitation, of cycloalkyl groups include cyclopropane, cyclobutane, cyclopentane, cyclopentene, cyclohexane, cyclohexadiene, cycloheptane, cycloheptatriene and adamantane.

As used herein, the term "aryl" describes an all-carbon monocyclic or fused-ring polycyclic (i.e., rings which share adjacent pairs of carbon atoms) groups having a completely conjugated pi-electron system. Examples, without limitation, of aryl groups include phenyl, naphthalenyl and anthracenyl.

According to one embodiment, the bond is an ester bond. As used herein throughout, the phrase "ester bond" encompasses any bond that includes a carboxy (C=O) or a thiocarboxy (C=S) group, such as, for example, a carboxylic ester bond, an oxyalkyl carboxylic ester bond, an amide bond, and a thioester bond, as these are defined herein. According to one embodiment, the bond is a carboxylic ester bond.

Such ester bonds are known to be hydrolizable by brain derived enzymes, such as esterases and amidases, and it is therefore suggested that the conjugates presented herein act as prodrugs capable of being metabolized in the brain to thereby release GABA (or a GABA compound) or glycine (or a glycine compound) within the target brain tissue. This process enables transporting GABA or a GABA compound) or glycine (or a glycine compound) across the blood-brain barrier conveniently, effectively and safely.

Such ester bonds can be readily formed by reacting a first compound (e.g., the first moiety, being a GAB compound or a glycine compound) that has a free carboxylic acid group, as defined herein, with a second compound (e.g., the second moiety, being an analgesic) that has a functional group which can react with the carboxylic acid, so as to form a corresponding ester bond. Such a functional group can be, for example, an amine (for forming an amide bond), a hydroxy (for forming a carboxylic ester bond), a thiol (for forming a thioester bond) or a chloroalkyl ester (for forming an oxyalkyl carboxylic ester bond).

Other bonds, linking the first and the second moieties, as described hereinabove, can be readily formed by reacting appropriate functional groups of each of the first and the second moieties or derivatives thereof. Thus, for example, a carbamate bond can be formed by reacting an isocyanate and an alcohol, a thiocarbamate bond can be formed by reacting a thioisocyanate and an alcohol, a urea bond can be formed by reacting an isocyanate and an amine, a thiourea bond can be formed by reacting a thioisocyanate and an amine, and an imine bond can be formed by reacting an aldehyde and an amine.

The term "free carboxylic acid" describes a —C(=O)—OH group, either as is, in its protonated state or in its ionized or salt state.

The term "amine" is used herein to describe a —NR'R" group, where R' and R" can be, for example, hydrogen, alkyl, cycloalkyl or aryl, as these terms are defined herein.

The term "halide" and "halo" describes fluorine, chlorine, bromine or iodine.

The term "haloalkyl" describes an alkyl group as defined above, further substituted by one or more halide(s).

The term "ester" describes a —C(=O)—O—R group, where R is alkyl, cycloalkyl or aryl.

The term "haloalkyl ester" describes a C(=O)—O—R group, where R is a haloalkyl group as defined herein.

The term "aldehyde" describes a —C(=O)—H group.

The term "hydroxyl" describes a —OH group.

The term "alkoxy" describes both an —O-alkyl and an —O-cycloalkyl group, as defined herein.

The term "aryloxy" describes both an —O-aryl and an —O-heteroaryl group, as defined herein.

The term "thiohydroxy" or "thiol" describes a —SH group.

The term "thioalkoxy" describes both a —S-alkyl group, and a —S-cycloalkyl group, as defined herein.

The term "thioaryloxy" describes both a —S-aryl and a —S-heteroaryl group, as defined herein.

The term "isocyanate" describes an —N=C=O group.

The term "thioisocyanate" describes an —N=C=S group.

The term "acyl halide" describes a —(C=O)R'''' group wherein R'''' is halide, as defined hereinabove.

The conjugates presented herein can therefore be readily prepared by coupling any first and second moieties that can react with one another, to thereby obtain a conjugate comprising these moieties linked therebetween. The nature of the bond linking the moieties is typically in accordance with the chemical nature of the second moiety. The chemical nature of the second moiety can be determined by the chemical nature of the analgesics or the analgesic derivative selected for composing the conjugate.

Thus, according to another aspect of the present invention there is provided a process of preparing a conjugate as described herein. This process is effected by reacting a first compound, being a GABA compound or a glycine compound, as described herein, and a second compound, being an analgesic or an analgesic derivative, as described herein.

GABA compounds as well as glycine compounds typically have a free carboxylic acid group, as defined herein. Hence, the process described herein may, according to one embodiment, include reacting a glycine compound or a GABA compound, having a free carboxylic group, with an analgesic or a derivative thereof that has a functional group that readily reacts with a carboxylic acid group. Further, the free carboxylic acid group may be activated, prior to the reaction. Such activation includes, for example, converting the free carboxylic group to an acyl halide derivative thereof.

Exemplary analgesics according to the present embodiments include acetaminophen, which includes a free hydroxy group, and opioids, which typically include a free hydroxy group.

Such analgesics can readily react with a compound that has a free carboxylic group, e.g., GABA or glycine, via a simple esterification. The resulting conjugates in each of these cases include these moieties that are linked to one another via a carboxylic ester bond.

Alternatively, various derivatives of the selected analgesic and/or the selected GABA compound or glycine compound, having other functional groups, can be utilized in the process, so as to form conjugates in which the first and the second moieties are linked to one another via other bonds, as is delineated herein.

In cases where the first moiety and the second moiety are linked via a carboxylic ester bond, synthesis of the conjugates presented herein may be effected by first converting the first compound into its corresponding acyl chloride derivative, or any other corresponding activated acyl derivative. The activated acyl derivative is thereafter reacted with an analgesic, which typically includes a free carboxylic acid group or hydroxy group, in a well-known nucleophilic-addition reaction, so as to obtain the desired conjugate having the second moiety covalently linked to the first moiety via a carboxylic ester bond. This reaction may be performed under basic conditions, so as to activate reactivity of the first compound and/or to neutralize compounds that are present as hydrochloride salts. It should be noted that the first compound and/or the second compound can be activated by any other known method.

In cases where the first moiety and the second moiety are linked via a thioester bond, the process of preparing the conjugates described herein may be effected by converting a second compound into its corresponding thiol derivative and converting the first compound into its corresponding acyl chloride derivative, or into any other activated derivative thereof. The thiol derivative is thereafter reacted with the activated first compound, by well-known procedures, so as to obtain the desired conjugate having the first moiety covalently linked to the second moiety via a thioester bond. It should be noted that in cases where the analgesic includes a free thiol group, it can be directly reacted with an acyl chloride derivative of the first compound. Analgesic drugs which do not include a free thiol group can be easily reacted so as to obtain a thiol derivative thereof, by methods well known in the art.

In cases where the first moiety and the second moiety are linked via an amide bond, the process of preparing the conjugates presented herein may be effected by first converting the first compound into its corresponding acyl chloride derivative, so as to activate the first compound and by further converting the second compound into an amine derivative thereof. The acyl chloride derivative is thereafter reacted with the amino group of the second compound, in a well-known nucleophilic-addition reaction, or by any other of the known procedures for producing an amide bond, so as to obtain the desired conjugate having the first moiety covalently linked to the second moiety via an amide bond. It should be noted that some analgesics include a free amine group and therefore such drugs can be directly reacted with an acyl chloride derivative of the first compound. Analgesic drugs which do not include a free amine group can be easily reacted so as to obtain an amine derivative thereof, by methods well-known in the art.

In cases where the first moiety and the second moiety are linked via an alkyloxy carboxylic ester bond, the process of preparing the conjugates presented herein may be effected by converting the second compound into a chloroalkyl ester derivative thereof. The chloroalkyl ester derivative is thereafter reacted with the first compound, in a well-known nucleophilic-addition reaction, or by any other of the known procedures for producing an alkyloxy carboxylic ester bond, so as to obtain the desired conjugate having the first moiety covalently linked to the second moiety via an alkyloxy carboxylic ester bond. It should be noted that covalently linking the first moiety and the second moiety via an alkyloxy carboxylic ester bond may be advantageous in cases where the second compound includes a free carboxylic acid group, since it avoids the formation of the typically unstable anhydride conjugate.

Since both glycine and most of the GABA compounds further have a free amine group, in any of the processes described hereinabove, the free amine group may be protected during the described reaction with the second compound. Protecting the free amino group is required since it is a relatively chemically active group, which can therefore undesirably participate in the reaction.

Hence, according to embodiments of the present invention, the process presented herein is effected by first protecting the free amine group of the first compound (e.g., GABA or glycine). Protecting the amine group can be performed by reacting the first compound with a known amine-protecting group such as, but not limited to, tert-butoxycarbonyl (Boc) and benzyloxycarbonyl (Cbz). The amino-protected first compound is then reacted with the analgesic drug, so as to obtain an amino-protected first moiety covalently linked to the analgesic drug. Once the reaction is completed, the protecting group can be removed.

Using the process described herein, radiolabeled conjugates can similarly be prepared, by using, for example, radiolabeled $^{14}$C-GABA or $^{14}$C-glycine as the first compound. Such radiolabeled conjugates can be efficiently utilized for determining the capacity of the conjugate to cross the blood-brain barrier (BBB) and to release GABA or glycine in brain tissues.

Thus, in an embodiment of the present invention, the conjugate presented herein can comprise, as the first moiety, a radiolabeled GABA compound or a radio labeled glycine compound.

In another embodiment of the present invention, such a radiolabeled compound can be prepared according to the process described herein, whereby the first compound is a radiolabeled compound such as, for example, $^{14}$C-GABA or $^{14}$C-glycine. Such a radiolabeled compound can be produced using standard methods known in the art.

Determining the concentration of a radiolabeled conjugate in blood and plasma and in the brain, and further determining the concentration of a radiolabeled GABA or a radiolabeled glycine released in these tissues, following administration of the conjugate, provide a straightforward determination of the efficiency of the conjugate to function as a carrier for delivering GABA or glycine into the brain.

Hence, according to another aspect of the present invention there is provided a method of determining a concentration of the conjugate described herein in a tissue of a subject. The method, according to this aspect of the present invention, is effected by administering to the subject a pre-determined amount of a radiolabeled conjugate as described herein; and determining a concentration of the radiolabeled conjugate and/or the radiolabeled first moiety in the tissue.

As used herein, the term "tissue" encompasses an organ tissue, as well as blood, plasma, and any other biological materials.

Since the conjugates of the present embodiments are aimed at crossing the BBB and release a GABA or glycine compound in a brain tissue, the method according to this aspect of the present invention is particularly useful for determining the concentration of the conjugate or of the GABA compound or the glycine compound (the first moiety) in the blood, the plasma and the brain. Thus, the ability of the conjugate to remain intact prior to crossing the BBB and to release a GABA or glycine compound in the brain can be determined.

Determining the concentration of the radiolabeled conjugate and/or the radiolabeled GABA compound or radiolabeled glycine compound can be effected by any of the methods known in the art for measuring radioactivity.

In an exemplary assay, the radiolabeled conjugate can be administered by oral gavage to laboratory animals, such as male Wistar rats. At designated time points (e.g., 0, 7.5 minutes, 15 minutes, 30 minutes, 60 minutes, 2 hours, 4 hours, 6 hours, 12 hours, 24 hours), rats are euthanized by asphyxiation with air/$CO_2$ gas followed by exsanguinations via the abdominal vein, from which blood and plasma are obtained. The brain is immediately harvested and snap-frozen and the radiolabeled conjugate is extracted from blood, serum, and brain tissue homogenates. Total radioactivity is assessed by liquid scintillation counting and tissue concentrations of $^{14}C$-GABA or $^{14}C$-glycine and the corresponding radiolabeled conjugate are analyzed by HPLC/radiodetector. Peaks are identified by co-elution (as relative retention time) with reference standards run under the same conditions in parallel.

The present invention further encompasses any pharmaceutically acceptable salt, solvate or hydrate of the conjugates described herein, as well as processes of preparing these pharmaceutically acceptable salts, solvates and hydrates.

The phrase "pharmaceutically acceptable salt" refers to a charged species of the parent compound and its counter ion, which is typically used to modify the solubility characteristics of the parent compound and/or to reduce any significant irritation to an organism by the parent compound, while not abrogating the biological activity and properties of the administered compound (herein, the conjugate).

The term "solvate" refers to a complex of variable stoichiometry (e.g., di-, tri-, tetra-, penta-, hexa-, and so on), which is formed by a solute (the conjugate) and a solvent, whereby the solvent does not interfere with the biological activity of the solute. Suitable solvents include, for example, ethanol, acetic acid and the like.

The term "hydrate" refers to a solvate, as defined hereinabove, where the solvent is water.

The present invention further encompasses various crystalline forms (polymorphs) of the conjugates described herein, as well as processes of preparing these crystalline forms.

The conjugates according to the present embodiments, by being capable of effectively crossing the BBB and releasing free GABA or glycine in the brain tissue, can be beneficially used in various therapeutic applications in which elevated levels of GABA or glycine in the brain are desired. These include, for example, treating or preventing CNS-associated diseases or disorders associated with low levels of GABA or glycine, reducing adverse side effects induced by psychotropic drugs, and/or enhancing the therapeutic efficacy of a psychotropic drug.

Hence, according to additional aspects of the present invention, any of the conjugates described herein can be used as a medicament, whereby the medicament can be utilized in any of the therapeutic applications described herein.

According to an additional aspect of the present invention there is provided a method of treating a CNS-associated disease or disorder. The method, according to this aspect of the present invention is effected by administering to a subject in need thereof a therapeutically effective amount of any of the conjugates described herein.

The term "treating" as used herein refers to abrogating, substantially inhibiting, slowing or reversing progression of a disease or disorder, substantially ameliorating clinical symptoms of a disease or disorder, substantially preventing the appearance of clinical symptoms of a disease or disorder, or substantially reducing adverse side effects of other drugs (e.g., psychotropic drugs) being administered.

The term "subject" as used herein refers to a mammal having a blood brain barrier, preferably a human being.

As used herein, the phrase "CNS-associated disease or disorder" encompasses any disease or disorder which is related to the central nervous system (CNS). Examples of CNS-associated diseases or disorders which are treatable using the conjugates of the present embodiments, include, but are not limited to, psychotic diseases or disorders, pain disorders, anxiety disorders, dissociative disorders, personality disorders, mood disorders, affective disorders, neurodegenerative diseases or disorders, cognitive disorders, convulsive disorders, boarder line disorders and mental diseases or disorders.

Conjugates that comprise a GABA compound are particularly beneficial for treating CNS-associated diseases and disorders that involve low levels of GABA in the brain. These include, for example, a pain disorder, a motion disorder, an anxiety disorder, a depression, a dissociative disorder, a mood disorder, an affective disorder, a neurodegenerative disease or disorder, a convulsive disorder, Parkinson's disease, Alzheimer's disease and epilepsy.

While, as described hereinabove, low levels of GABA have been associated with epileptic seizures, motion disorders such as Parkinson's disease, Multiple Sclerosis, action tremors and tardive dyskinesia, and mood disorders such as panic, anxiety, depression, alcoholism and manic behavior, the conjugates described herein So in which the first moiety is a GABA compound are particularly useful for treating these diseases and disorders.

Conjugates that comprise a glycine compound are particularly beneficial for treating CNS-associated diseases and disorders in which binding of glycine to strychnine-sensitive and strychnine-insensitive binding sites in the brain is beneficial. These include, for example, psychotic disorders such as schizophrenia, motion disorders, neurodegenerative diseases and disorders, convulsive disorders, and cognitive disorders.

While, as described hereinabove, administration of glycine was found highly beneficial in the treatment of schizophrenia, epileptic seizures, Alzheimer's disease, and in improving learning and cognition, the glycine-containing conjugates described herein are particularly useful for treating these diseases and disorders.

In addition, since the conjugates described herein are capable of releasing, upon penetrating the brain, an analgesic moiety in addition to the GABA or glycine compound, the conjugates, by combining the analgesic effect of both the analgesic drug and the GABA or glycine compound, are further particularly useful for treating pain, and more particularly, neuropathic pain.

As is further discussed in detail hereinabove, GABA (including any GABA compound as described herein) and glycine (including any glycine compound as described herein) can be further beneficially used in combination with CNS-acting agents. It has been shown that a GABA compound, when used in combination with, for example, a psychotropic drug, can reduce adverse side effected induced by the drug and can further enhance the therapeutic efficacy of the drug. It has been further shown that glycine, when used in combination with, for example, a psychotropic drug, can reduce adverse side effected induced by the drug and can further enhance the therapeutic efficacy of the drug.

The conjugates described herein can therefore be beneficially used in a combined treatment that further includes administration of a CNS-acting agent.

Thus, according to an additional aspect of the present invention there is provided a method of reducing a side effect induced by a CNS-acting agent.

According to yet an additional aspect of the present invention there is provided a method of enhancing the therapeutic efficacy of a CNS-acting agent.

Each of the methods according to these aspects of the present invention is effected by administering to a subject in need thereof, in combination with the CNS-acting agent, a therapeutically effective amount of a conjugate as described herein.

The methods according to these aspects of the present invention are highly advantageous since the amount of the conjugate, the route of administering the conjugate and the time and regime for its administration can be independently optimized, regardless of the corresponding parameters for administering the CNS-acting agent.

Thus, in each of the methods according to these aspects of the present invention, the conjugate can be administered either prior to, concomitant with or subsequent to administering the CNS-acting agent.

The therapeutically effective amount of the conjugate, as defined hereinbelow, can be determined, depending on the CNS-acting agent used and the desired activity, so as to result with an optimal activity of the conjugate.

In addition, in each of the methods according to these aspects of the present invention, the conjugate can be utilized as a part of a pharmaceutical composition, as described in detail hereinbelow. In particular embodiments, where the conjugate is administered concomitant with the CNS-acting agent, both the conjugate and the CNS-acting agent can form a part of the same pharmaceutical composition, as is further detailed hereinbelow.

As used herein, the phrase "CNS-acting agent" encompasses any compound which is capable of exerting a CNS activity.

The phrase "CNS activity" as used herein describes a pharmacological activity exerted in the CNS, which is aimed at treating a CNS-associated impairment. Such a pharmacological activity typically includes modulation of neuronal signals transduction.

According to one embodiment, the CNS-acting agent is a psychotropic drug.

Psychotropic drugs are known in the art, and are referred to herein, as pharmacological agents that exert activity in the CNS to thereby treat a CNS-associated disease or disorder.

Psychotropic drugs include, but are not limited to, antipsychotic drugs (typical and atypical), anxiolytic drugs, anti-depressants, anti-convulsive drugs (also referred to herein and is the art and anti-convulsants), anti-parkinsonian drugs, acetylcholine esterase inhibitors, MAO inhibitors, selective serotonin reuptake inhibitors (SSRIs) and selective noradrenalin receptor inhibitors (SNRIs).

Representative examples of psychotropic drugs that can be utilized in combination with the conjugates of the present embodiments include, without limitation, chlorpromazine, perphenazine, fluphenazine, zuclopenthixol, a thiopropazate, haloperidol, benperidol, bromperidol, droperidol, spiperone, pimozide, piperacetazine, amilsulpride, sulpiride, clothiapine, ziprasidone, remoxipride, sultopride, alizapride, nemonapride, clozapine, olanzapine, ziprasidone, sertindole, quetiapine, fluoxetine, fluvoxamine, desipramine, paroxetine, sertraline, valproic acid, temazepam, flutemazepam, doxefazepam, oxazepam, lorazepam, L-dopa, lormetazepam, cinolazepam, flutazolam, lopirazepam, meprobamate, carisoprodol, acetophenazine, carphenazine, dixyrazine, priciazine, pipothiazine, homophenazine, perimetazine, perthipentyl, flupentixol, piflutixol, teflutixol, oxypethepin, trifluperidol, penfluridol, meclobemide, norclomipramine, amoxapine, nortriptyline, protriptyline, reboxetine, tacrine, rasagiline, amantidine, duloxetine, phenobarbital, phenyloin, phenothiazine, benzodiazepine and butyrophenone.

The phrase "side effects" as used herein refers to adverse symptoms that may develop as a result of administering to a subject a certain drug and particularly a psychotropic drug.

Representative examples of adverse side effects often associated with use of psychotropic drugs include, but not limited to, rigidity, tremor, bradykinesia, bradyphrenia, tardive dyskinesia, catalepsy, acute dystonic reactions and akathasia.

The phrase "enhanced therapeutic activity" as used herein describes a CNS activity as defined herein, exerted upon concurrent use of a conjugate as described herein and a CNS-acting agent, which is higher than that of the CNS-acting agent when administered alone. Such an enhanced therapeutic activity is typically characterized by reduced effective concentrations of the CNS-acting agent that are required to achieve a certain therapeutic activity.

The phrase "enhanced therapeutic activity" as used herein further describes a CNS activity as defined herein, exerted upon concurrent use of a conjugate as described herein and a CNS-acting agent, which is accompanied by an additional therapeutic activity and thus by an added therapeutic value such as, for example, increased GABA activity, pain relief and the like. Without being bound to any particular theory, it is assumed that the enhanced therapeutic activity results, at least in part, from an improved balance of neurotransmitters in the brain that is achieved by the combined treatment of the conjugates described herein and a CNS-acting agent.

A treatment that combines a conjugate as described herein and a CNS-acting agent can therefore be advantageously utilized in methods of treating any CNS-associated diseases and disorders.

Thus, according to still an additional aspect of the present invention, there is provided a method of treating a CNS-associated disease or disorder, as defined herein. The method, according to this aspect of the present invention, is effected by administering to a subject in need thereof a therapeutically effective amount of a conjugate according to the present embodiments and a therapeutically effective amount of a CNS-acting agent. The conjugate can be administered prior to, concomitant with or subsequent to administering the CNS-acting agent.

Any of the CNS-associated diseases or disorders delineated hereinabove can be treated by this method, upon selecting an appropriate CNS-acting agent.

Examples of such CNS-associated diseases or disorders include, but are not limited to, neuropathic pain, schizophrenia, paranoia, childhood psychoses, Huntington's disease, Gilles de la Tourette's syndrome, depression, manic depression, anxiety, Parkinson's disease, Alzheimer's disease and epilepsy.

In each of the methods described herein, the phrase "therapeutically effective amount" refers to that amount of the conjugate being administered which is capable of (i) relieving to some extent one or more of the symptoms of the CNS-associated disease or disorder being treated, (ii) reducing to some extent one or more of the adverse side effects induced by a CNS-acting agent, and/or (iii) enhancing the therapeutic activity of the CNS-acting agent, as is discussed in detail hereinunder.

The phrase "therapeutically effective amount", when used in the context of a CNS-acting agent, refers to that amount of the CNS-acting agent which is capable of relieving to some extent one or more of the symptoms of the CNS-associated disease or disorder being treated.

A therapeutically effective amount of the conjugate, according to embodiments of this aspect of the present invention, preferably ranges from about 0.01 to about 50 mg/kg body, more preferably from about 0.05 to about 25 mg/kg body, more preferably from about 0.1 to about 10 mg/kg body, and more preferably from about 0.2 to about 5 mg/kg body.

In each of the methods described herein, the conjugate can be administered by any acceptable route of administration. According to one embodiment, the conjugate is administered parenterally or orally.

In each of the methods described herein, the conjugate can be utilized either as is, or, can form a part of a pharmaceutical composition, as mentioned hereinabove.

Hence, according to a further aspect of the present invention there is provided a pharmaceutical composition which comprises, as an active ingredient, any of the conjugates described herein and a pharmaceutically acceptable carrier.

As used herein, a "pharmaceutical composition" refers to a preparation including the conjugate, as described herein; and other chemical components such as physiologically suitable carriers and excipients. The purpose of a pharmaceutical composition is to facilitate administration of a compound to an organism.

Hereinafter, the term "pharmaceutically acceptable carrier" refers to a carrier or a diluent that does not cause significant irritation to a subject and does not abrogate the biological activity and properties of the administered compound. Examples, without limitations, of carriers are propylene glycol, saline, emulsions and mixtures of organic solvents with water.

Herein the term "excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, transdermal, intestinal or parenteral delivery, including intramuscular, subcutaneous and intramedullary injections as well as intrathecal, direct intraventricular, intravenous, intraperitoneal, intranasal, or intraocular injections. Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more pharmaceutically acceptable carriers comprising excipients and auxiliaries, which facilitate processing of the active compounds into preparations which can be used pharmaceutically. Proper formulation is dependent upon the route of administration chosen.

For injection, the conjugates of the invention may be formulated in aqueous solutions, preferably in physiologically compatible buffers such as Hank's solution, Ringer's solution, or physiological saline buffer with or without organic solvents such as propylene glycol, polyethylene glycol. For transmucosal administration, penetrants are used in the formulation. Such penetrants are generally known in the art.

For oral administration, the conjugates of the invention can be formulated readily by combining the active compounds with pharmaceutically acceptable carriers well known in the art. Such carriers enable the conjugates of the invention to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethylcellulose, sodium carbomethylcellulose and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the conjugates may take the form of tablets or lozenges formulated in conventional manner.

For administration by inhalation, the compositions for use according to the present invention are conveniently delivered in the form of an aerosol spray presentation from a pressurized pack or a nebulizer with the use of a suitable propellant, e.g., dichlorodifluoromethane, trichlorofluoromethane, dichlorotetrafluoroethane or carbon dioxide. In the case of a pressurized aerosol, the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

The conjugates described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active compound in water-soluble form. Additionally, suspensions of the active compounds may be prepared as appropriate oily injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the conjugates to allow for the preparation of highly concentrated solutions.

Alternatively, the active ingredient may be in powder form for constitution with a suitable vehicle, e.g., sterile, pyrogen-free water, before use.

The conjugates of the present invention may also be formulated in rectal compositions such as suppositories or retention enemas, using, e.g., conventional suppository bases such as cocoa butter or other glycerides.

The pharmaceutical compositions herein described may also comprise suitable solid of gel phase carriers or excipients. Examples of such carriers or excipients include, but are not limited to, calcium carbonate, calcium phosphate, various sugars, starches, cellulose derivatives, gelatin and polymers such as polyethylene glycols.

Pharmaceutical compositions suitable for use in context of the present invention include the active ingredients contained in an amount effective to achieve the intended purpose. More specifically, a therapeutically effective amount means an amount of conjugate effective to prevent, alleviate or ameliorate symptoms of CNS-associated disease or disorder or to reduce the adverse side effects induced by the CNS-acting agent.

Determination of a therapeutically effective amount is well within the capability of those skilled in the art, especially in light of the detailed disclosure provided herein.

For any conjugate used in the methods of the invention, the therapeutically effective amount or dose can be estimated initially from activity assays in cell cultures and/or animals. For example, a dose can be formulated in animal models to achieve a circulating concentration range that includes the IC50 as determined by activity assays (e.g., the concentration of the test compound, which achieves a half-maximal activity in the GABA system). Such information can be used to more accurately determine useful doses in humans.

Toxicity and therapeutic efficacy of the conjugates described herein can be determined by standard pharmaceutical procedures in experimental animals, e.g., by determining the IC50 and the LD50 (lethal dose causing death in 50% of the tested animals) for a subject compound. The data obtained from these activity assays and animal studies can be used in formulating a range of dosage for use in human.

The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide plasma levels of the active moiety which are sufficient to maintain the psychotropic effects and/or to avert the adverse side effects of psychotropic drugs, termed the minimal effective concentration (MEC). Dosages necessary to achieve the MEC will depend on individual characteristics and route of administration. HPLC assays or bioassays can be used to determine plasma concentrations.

Dosage intervals can also be determined using the MEC value. Preparations should be administered using a regimen, which maintains plasma levels above the MEC for 10-90% of the time, preferable between 30-90% and most preferably 50-90%.

Depending on the severity and responsiveness of the condition to be treated, dosing can also be a single administration of a controlled released formulation.

The phrase "controlled release" as used herein refers to a formulation capable of releasing the active ingredient at a predetermined rate such that therapeutically beneficial levels are kept over an extended period of time. Suitable controlled release formulations are well known in the art (e.g., "Remington's Pharmaceutical Sciences," Philadelphia College of Pharmacy and Science, 19th Edition, 1995).

The amount of a pharmaceutical composition to be administered will, of course, be dependent on the subject being treated, the severity of the affliction, the manner of administration, the judgment of the prescribing physician, etc.

According to an embodiment of the present invention, the pharmaceutical composition further comprises a CNS-acting drug. The conjugate and the CNS-acting agent can be provided within such a pharmaceutical composition in a molar ratio that ranges, respectively, from about 1:100 to about 100:1, from about 1:50 to about 50:1, from about 1:20 to about 20:1, from about 1:10 to about 10:1, from about 1:5 to about 5:1, from about 1:2 to about 2:1, or is about 1:1.

Such a pharmaceutical composition can be further formulated so as to independently release each of the active ingredients at a predetermined rate. Thus, for example, the pharmaceutical composition can be formulated as a core-shell capsule in which an active ingredient in the shell is further released, followed by a timely-controlled release of the active ingredient in the core.

Any of the pharmaceutical compositions of the present invention may, if desired, be presented in a pack or dispenser device, such as a FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Pharmaceutical compositions comprising the conjugate of the invention, optionally in combination with a CNS-acting agent, formulated in a compatible pharmaceutical carrier may also be prepared, placed in an appropriate container, and labeled for treatment of an indicated condition, as set forth hereinabove.

Thus, according to an embodiment of this aspect of the present invention, the pharmaceutical composition is packaged in a packaging material and identified in print, in or on the packaging material, for use in the treatment of a CNS-associated disease or disorder, for reducing side effects induced by a psychotropic drug and/or for enhancing the therapeutic efficacy of a psychotropic drug, as described herein.

Such a packaged pharmaceutical composition is also referred to herein interchangeably as an article-of-manufacturing.

In cases where the pharmaceutical composition comprises a conjugate and a CNS-acting drug, the conjugate and the CNS-acting agent can be jointly contained within a single object (e.g., a tablet or a capsule), or separately within different objects.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below.

Example 1

Synthesis of Acetaminophen-GABA Conjugate (HCl Salt)

Route I

The preparation of an HCl salt of an acetaminophen-GABA conjugate (also denoted herein as BL-1022 HCl salt or 4-acetamidophenyl 4-aminobutanoate hydrochloride) is depicted in Scheme 1 below.

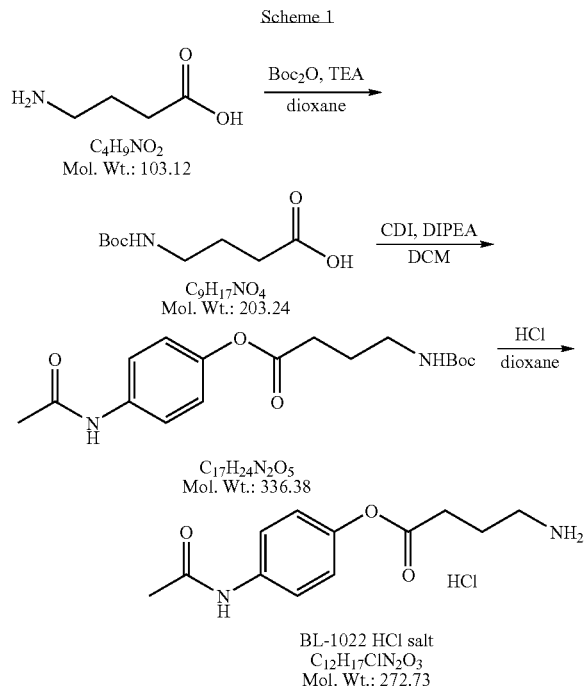

Materials and Methods:

4-aminobutyric acid (GABA), N-(4-hydroxyphenyl)acetamide (acetaminophen), carbonyldiimidazole (CD1), and N-ethyldiisopropylamine (DIPEA) were purchased from Sigma. All other reagents and solvents were obtained from known vendors.

HPLC analyses were performed on a system equipped with a Nucleosil C18 column (25×4.6 mm), and a UV detector operated at 245 nm, using a 1:1 $CH_3CN$:buffer as a mobile phase at 1 ml/minute.

NMR measurements were performed on a 300 MHz AVF 949 BF, using DMSO as a solvent.

Water content was measured using Karl-fisher titration.

Chlorine content was determined by Shapiger's method together with mercurrometrical analysis end (titrant: $Hg(NO_3)_2$ 0.01328 H.

Synthesis:

A 6-liter three-necked round bottom flask equipped with a cooling bath and a thermometer was charged with 4-aminobutyric acid (167 grams, 1.62 moles) in dioxane (1 liter) and water 0.5 liter). Triethylamine (450.5 ml, 3.24 moles) was then added and the mixture was stirred for 20 minutes at 10° C. Boc anhydride (353.2 grams, 1.62 moles) was thereafter added at 15° C. and the resulting mixture was stirred for 12 hours at 17° C. Then, 0.5N HCl (5 liters) was added and the product (the organic phase) was extracted with ethyl acetate. The extract phase was washed with brine, dried over $MgSO_4$ overnight and the solvent was evaporated under reduced pressure to afford 300 grams of the N-Boc-protected GABA (91% yield). The compound's structure was confirmed by $^1$H-NMR.

A 12-liters three-necked round bottom flask equipped with a nitrogen inlet, a thermometer, a mechanical stirrer and an additional funnel was charged with N-boc-protected GABA (422 grams, 2.08 moles) in dichloromethane (DCM, 6 liters). Carbonyl diimidazole (CDI, 337.3 grams, 2.08 moles) was added dropwise at 17° C., while stirring and the resulting mixture was further stirred for 3 hours. N-(4-hydroxyphenyl) acetamide (acetaminophene, 314.5 grams, 2.08 moles) was then added, the mixture was stirred for 20 minutes and N-ethyldiisopropylamine (DIPEA, 359.8 grams, 2.08 moles) was added. The resulting mixture was stirred for 24 hours at 17° C., and was thereafter consecutively washed in a separation funnel with 0.1N HCl (2×5 liters), 0.1N NaOH (2×5 liters) and water (2×5 liters). The organic phase was dried over $MgSO_4$ overnight and the solvent was evaporated under reduced pressure. The crude product was recrystallized from ethyl acetate (5 liters) to afford 437 grams (62% yield) of the N-boc-protected acetaminophen-GABA conjugate. The compound's structure was confirmed by $^1$H-NMR.

A 12-liters three-necked round bottom flask equipped with a nitrogen inlet, a thermometer, a mechanical stirrer and an additional funnel was charged with N-boc-protected acetaminophen-GABA conjugate (437 grams, 1.3 moles) in dichloromethane (DCM, 5 liters). The mixture was stirred for 1 hour and was thereafter cooled to 10° C. 4M HCl (975 ml, 3.9 moles) was then added at 0° C. while stirring and the mixture was stirred for 15 hours at 17° C. The obtained solid was then filtered put, washed with DCM (3×3 liters) and dried in an over at 55° C. for 20 hors, to afford 350 grams (98% yield) of the final product, the HCl salt of acetaminophen-GABA conjugate (BL-1022 HCl salt), having a purity of 99.3%, as determined by HPLC. Excess HCl was removed by recrystallization from methanol.

Product Characterization:

Elemental Analysis: C, 52.96; H, 6.25; N, 10.36.

Chlorine content: 13.2% (±0.1%).

The water content of the product remained substantially unchanged upon sitting in vial (uncapped) on the bench overnight (0.15% vs. 0.16%).

The stability of BIL-1022 was briefly studied. BIL-1022 is stable in water and methanol at low pH (3-5) at room temperature (20-25° C.).

Example 2

Synthesis of Acetaminophen-GABA Conjugate

Route II

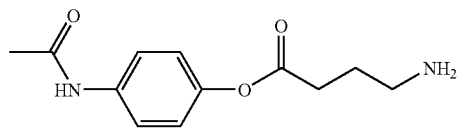

An acyl chloride derivative of γ-aminobutyric acid (GABA) is prepared by mixing one equivalent of γ-aminobutyric acid (GABA) with thionyl chloride (20 equivalents) followed by addition of few drops of dimethylformamide (DMF; catalytic amount) to start the reaction. The reaction is refluxed for about 3 to 4 hr, and then the thionyl chloride is distilled out under vacuum to obtain the acyl chloride derivative of GABA.

A mixture of the acetaminophen (1 equivalent), an acyl chloride derivative of GABA (1.1 equivalents) and, optionally, $Et_3N$ (2 equivalents; used to free starting materials found as their HCl salts) is stirred in 5-10 ml DMF at room temperature, under nitrogen atmosphere, for 24 hours. The mixture is then extracted with ethyl acetate and water. The organic layer is thereafter washed with 5% $NaHCO_3$ and brine, dried over $MgSO_4$, filtered and evaporated, to thereby generate the acetaminophen-GABA conjugate.

Example 3

Synthesis of Acetaminophen-Glycine Conjugate

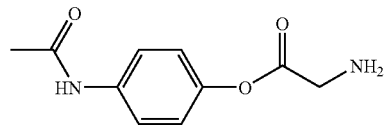

An acyl chloride derivative of glycine is prepared by mixing one equivalent of glycine with thionyl chloride (20 equivalents) followed by addition of few drops of dimethylformamide (DMF; catalytic amount) to start the reaction. The reaction is refluxed for about 3 to 4 hr, and then the thionyl chloride is distilled out under vacuum to obtain the acyl chloride derivative of glycine.

A mixture of the acetaminophen (1 equivalent), an acyl chloride derivative of glycine (1.1 equivalents) and, optionally, $Et_3N$ (2 equivalents; used to free starting materials found as their HCl salts) is stirred in 5-10 ml DMF at room temperature, under nitrogen atmosphere, for 24 hours. The mixture is then extracted with ethyl acetate and water. The organic layer is thereafter washed with 5% $NaHCO_3$ and brine, dried over $MgSO_4$, filtered and evaporated, to thereby generate the acetaminophen-glycine conjugate.

Example 4

Synthesis of Codeine-GABA Conjugate

The preparation of a HCl salt of a codeine-GABA conjugate (also denoted herein as NL-I-123) is depicted in Scheme 2 below.

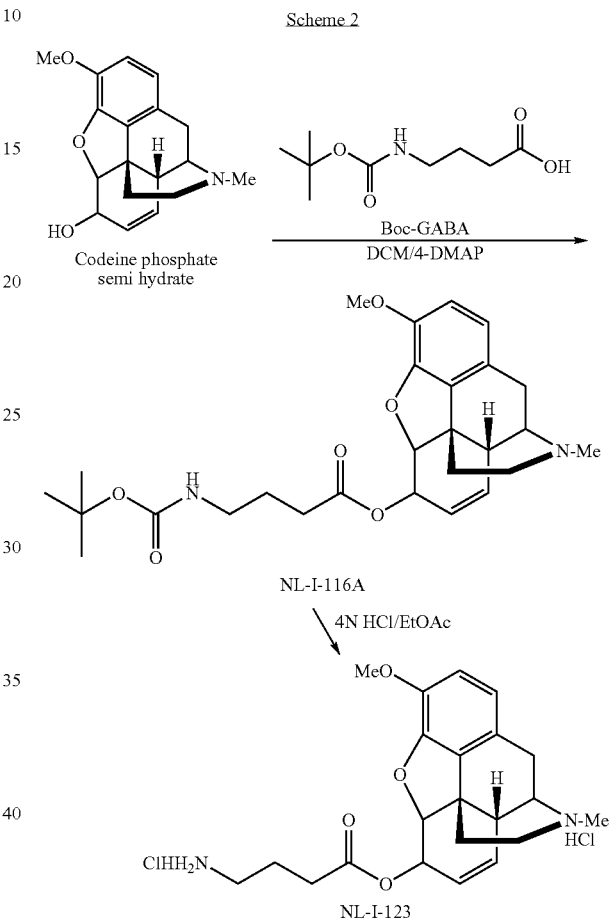

Preparation of NL-I-116A:

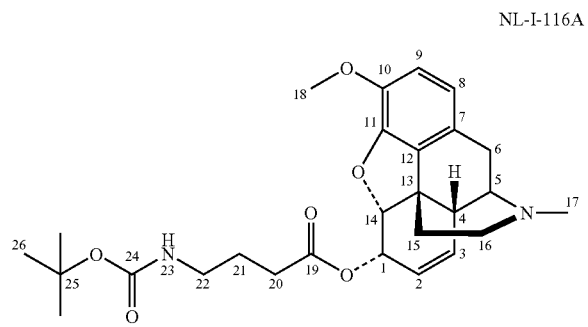

To an ice-cold stirred solution of N-Boc-protected GABA (250 mg, 1.23 mmol) in dry $CH_2Cl_2$ (12.5 ml), (3-dimethylaminopropyl)-3-ethylcarbodiimide hydrochloride (EDC, 260 mg, 1.35 mmol) and 4-dimethylaminopyridine (4-DMAP) (150 mg, 1.35 mmol) were added. After 1 hour the ice bath was removed and codeine phosphate semi hydrate (500 mg, 1.23 mmol) and 4-DMAP (410 mg, 3.69 mmol) were added. After 3 days the solids were filtered and the filtrate was evaporated. The residue was purified by silica gel chromatography (using a mixture of 10:1.5 $CHCl_3$:MeOH as eluent), to give NL-I-116A (273 mg, 45.7% yield).

$^1$H-NMR (600 MHz, $CDCl_3$): δ=6.68 (d, J=9.0 Hz, 1H, H-8), 6.57 (d, J=9.0 Hz, 1H, H-9), 5.66 (dm, J=9.0 Hz, H, 1H-2), 5.43 (dm, J=9 Hz, 1H, H-3), 5.20 (m, 1H, H-1), 5.13 (d, J=6 Hz, 1H, H-14), 5.08 (m, 1H), 3.85 (s, 3H, H-18), 3.46 (m, 1H), 3.26 (m, 1H), 3.20 (m, 1H), 3.05 (d, J=24 Hz, 1H), 2.93 (m, 1H), 2.71 (m, 1H), 2.52-2.38 (m, 7H), 2.15 (m, 1H), 1.9 (m, 3H), 1.44 (s, 9H, H-26) ppm.

$^{13}$C-NMR (600 MHz, $CDCl_3$), δ=172.69 (1C, C-19), 156.08 (1C, C-24), 146.56 (1C, C-11), 142.39 (1C, C-10), 130.20 (1C, C-12), 128.86 (2C, C-2+C-3), 126.01 (1C, C-7), 119.32 (1C, C-8), 113.52 (1C, C-9), 87.59 (1C, C-14), 79.04 (1C, C-25), 67.85 (1C, C-1), 59.43 (1C, C-5), 56.38 (1C, C-18), 46.86 (1C, C-16), 42.76 (1C, C-17), 42.30 (1C, C-13)$_3$ 39.94 (1C, C-4), 39.79 (1C, C-22), 34.82 (1C, C-15), 31.29 (1C, C-20), 28.48 (3C, C-26), 25.18 (1C, C-21), 20.61 (1C, C-6) ppm.

Preparation of NL-I-123:

NL-I-123

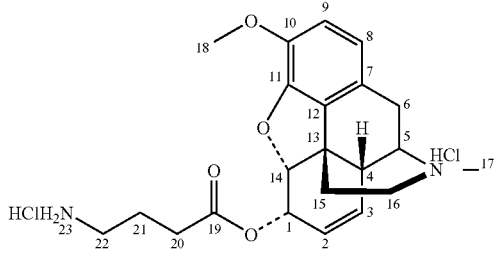

NL-I-116A (250.7 mg, 0.52 mmol) was dissolved and stirred in a freshly prepared 4N HCl/EtOAc solution (20 ml) for 1 hour. The solvent was thereafter evaporated to give the product as a white solid (231.6 mg, 97% yield).

$^1$H-NMR (600 MHz, $D_2O$): δ=6.95 (d, J=9.19 Hz, 1H, H-8), 6.83 (d, J=9.19 Hz, 1H, H-9), 5.77 (dm, J=10.79 Hz, 1H, H-2), 5.61 (dm, J=10.79 Hz, 1H, H-3), 5.31 (m, 2H, 1H-1+H-14), 4.24 (m, 1H, H-5), 3.85 (s, 3H, H-18), 3.36 (m, 1H, H-16), 3.30 (m, 1H, H-6), 3.2-2.8 (m, 8H, H-4+H-6, H-16, H-17+H-22), 2.60 (m, 2H, H-20), 2.36-2.09 (m, 1H, H-15), 2.01 (m, 2H, H-21) ppm.

$^{13}$C-NMR (600 MHz, $D_2O$): δ=174.18 (1C, C-19), 146.01 (1C, C-11), 142.96 (1C, C-10), 129.87 (1C, C-2), 129.09 (1C, C-7 or c-12), 127.18 (1C, C-3), 124.55 (1C, C-7 or C-12), 121.60 (1C, C-8), 115.33 (1C, C-9), 87.33 (1C, C-14), 68.16 (1C, C-1), 61.50 (1C, C-5), 57.14 (1C, C-18), 48.40 (1C, C-16), 41.61 (1C, C-17), 41.22 (1C, C-13), 39.42 (1C, C-12), 38.77 (1C, C-4), 32.91 (1C, C-15), 31.05 (1C, C-20), 22.61 (1C, C-21), 21.35 (1C, C-6) ppm.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof it is evident that many alternatives, modifications and variations will be apparent to those skilled in the art. Accordingly, it is intended to embrace all such alternatives, modifications and variations that fall within the spirit and broad scope of the appended claims. All publications, patents, patent applications mentioned in this specification are herein incorporated in their entirety by reference into the specification, to the same extent as if each individual publication, patent, patent application was specifically and individually indicated to be incorporated herein by reference. In addition, citation or identification of any reference in this application shall not be construed as an admission that such reference is available as prior art to the present invention.

What is claimed is:

1. A conjugate comprising a first moiety being covalently linked to a second moiety, wherein said first moiety is γ-aminobutyric acid (GABA) and said second moiety is acetaminophen, the conjugate having the formula:

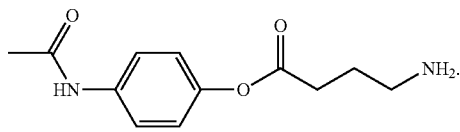

2. A pharmaceutical composition comprising, as an active ingredient, the conjugate of claim 1 and a pharmaceutically acceptable carrier.

3. The pharmaceutical composition of claim 2, further comprising a CNS-acting agent wherein the CNS-acting agent is a psychotropic drug.

4. The pharmaceutical composition of claim 2, being packaged in a packaging material and identified in print, in or on said packaging material, for use in the treatment of a CNS-associated disease or disorder, for reducing side effects induced by a psychotropic drug and/or for enhancing the therapeutic efficacy of a psychotropic drug wherein the CNS-associated disease or disorders involve low levels of GABA in the brain.

5. An article-of-manufacturing comprising the pharmaceutical composition of claim 3, being packaged in a packaging material and identified in print, on or in said packaging material, for use in the treatment of a CNS-associated disease or disorder, for reducing side effects induced by a CNS-acting agent and/or for enhancing the therapeutic efficacy of a CNS-acting agent wherein the CNS-acting agent is a psychotropic drug.

6. The article-of-manufacturing of claim 5, wherein said conjugate and said CNS-acting agent are jointly contained within a single object.

7. The article-of-manufacturing of claim 6, wherein said single object is a tablet or a capsule.

8. The article-of-manufacturing of claim 5, wherein said conjugate and said CNS-acting agent are separately contained within different objects.

9. The article-of-manufacturing of claim 8, wherein each of said objects is independently a tablet or a capsule.

10. A method of treating a CNS-associated disease or disorder, the method comprising administering to a subject in need thereof a therapeutically effective amount of the conjugate of claim 1, thereby treating the CNS-associated disease or disorder wherein the CNS-associated disease or disorders involve low levels of GABA in the brain.

11. A method of reducing an adverse side effect induced by a CNS-acting agent, the method comprising administering to a subject in need thereof, in combination with the CNS-acting agent, a therapeutically effective amount of the conjugate of claim 1, thereby reducing the adverse side effect induced by the CNS-acting agent wherein the CNS-acting agent is a psychotropic drug.

12. The method of claim 11, wherein said conjugate forms a part of a pharmaceutical composition which further comprises a pharmaceutically acceptable carrier.

13. The method of claim 12, wherein said pharmaceutical composition further comprises the CNS-acting agent.

14. The method of claim 11, wherein said conjugate is administered prior to, concomitant with or subsequent to administering the CNS-acting agent.

15. The method of claim 11, wherein said adverse side effect is selected from the group consisting of rigidity, tremor, bradykinesia, bradyphrenia, tardive dyskinesia, catalepsy, acute dystonic reactions and akathasia.

16. A method of enhancing the therapeutic activity of a CNS-acting agent, the method comprising administering to a subject in need thereof, in combination with the CNS-acting agent, a therapeutically effective amount of the conjugate of claim 1, thereby enhancing the therapeutic activity of the CNS-acting agent wherein the CNS-acting agent is a psychotropic drug.

17. The method of claim 16, wherein said conjugate forms a part of a pharmaceutical composition that further comprises a pharmaceutically acceptable carrier.

18. The method of claim 17, wherein said pharmaceutical composition further comprises the CNS-acting agent.

19. The method of claim 16, wherein said conjugate is administered prior to, concomitant with or subsequent to administering the CNS-acting agent.

20. A method of treating a CNS-associated disease or disorder, the method comprising administering to a subject in need thereof a therapeutically effective amount of a CNS-acting agent and a therapeutically effective amount of the conjugate of claim 1 wherein the CNS-associated disease or disorders involve low levels of GABA in the brain and wherein the CNS-acting agent is a psychotropic drug.

21. The method of claim 20, wherein said conjugate is administered prior to, concomitant with or subsequent to administering the CNS-acting agent.

22. The method of claim 20, wherein said CNS-associated disease or disorder is selected from the group consisting of an anxiety disorder, a dissociative disorder, a mood disorder, an affective disorder, a neurodegenerative disease or disorder, and a convulsive disorder.

23. The method of claim 20, wherein said CNS disorder or disease is selected from the group consisting of depression, anxiety, Parkinson disease, Alzheimer disease and epilepsy.

\* \* \* \* \*